(12) United States Patent
Mizuguchi

(10) Patent No.: US 9,921,149 B2
(45) Date of Patent: Mar. 20, 2018

(54) OPTICAL MEASUREMENT APPARATUS AND OPTICAL MEASUREMENT METHOD

(71) Applicant: Otsuka Electronics Co., Ltd., Osaka (JP)

(72) Inventor: Tsutomu Mizuguchi, Ritto (JP)

(73) Assignee: Otsuka Electronics Co., Ltd., Osaka (JP)

( * ) Notice: Subject to any disclaimer, the term of this patent is extended or adjusted under 35 U.S.C. 154(b) by 198 days.

(21) Appl. No.: 15/027,536

(22) PCT Filed: Apr. 24, 2015

(86) PCT No.: PCT/JP2015/062472
§ 371 (c)(1),
(2) Date: Apr. 6, 2016

(87) PCT Pub. No.: WO2016/170667
PCT Pub. Date: Oct. 27, 2016

(65) Prior Publication Data
US 2017/0102321 A1    Apr. 13, 2017

(51) Int. Cl.
| | | |
|---|---|---|
| G01N 33/00 | (2006.01) | |
| G01N 21/27 | (2006.01) | |
| G01N 21/25 | (2006.01) | |

(52) U.S. Cl.
CPC ............ *G01N 21/27* (2013.01); *G01N 21/255* (2013.01); *G01N 33/00* (2013.01);
(Continued)

(58) Field of Classification Search
CPC ......... H01L 27/14612; H01L 27/14603; H01L 27/14609; H01L 27/14621;
(Continued)

(56) References Cited

U.S. PATENT DOCUMENTS 9,727,052 B2 *  8/2017  Price .................. G01J 3/28

FOREIGN PATENT DOCUMENTS

| JP | H02-134542 A | 5/1990 |
|---|---|---|
| JP | 2007-107053 A | 4/2007 |

(Continued)

OTHER PUBLICATIONS

International Search Report; PCT/JP2015/062472 dated Jul. 21, 2015.

*Primary Examiner* — Renee Chavez
(74) *Attorney, Agent, or Firm* — Studebaker & Brackett PC

(57) ABSTRACT

A controller of an optical measurement apparatus causes, in a condition that a rotational speed of a rotary body is controlled so that the speed is a specified value, a light source to generate light having a constant intensity and apply the light to an irradiation region, and acquires first timing information based on a change with time of an intensity of reflected light or transmitted light that is output from a second detection unit receiving the reflected light or transmitted light of the applied light. The controller causes the light source to periodically generate pulsed light in accordance with the first timing information and apply the pulsed light to the irradiation region, and acquires second timing information based on a result which is output from the first detection unit whose measurement is periodically enabled in accordance with the first timing information.

14 Claims, 18 Drawing Sheets

(52) U.S. Cl.
 CPC ............... *G01N 2033/0096* (2013.01); *G01N 2201/0826* (2013.01); *G01N 2201/0833* (2013.01)

(58) Field of Classification Search
 CPC ......... H01L 27/14623; H01L 27/14636; H01L 27/14645; H01L 27/14665; H01L 27/307; H01L 29/16; H01L 29/24; H01L 29/7869; H04N 5/361; H04N 5/369; H04N 5/374
 See application file for complete search history.

(56) References Cited

FOREIGN PATENT DOCUMENTS

| | | |
|---|---|---|
| JP | 2013-019854 A | 1/2013 |
| JP | 2014-066619 A | 4/2014 |

\* cited by examiner

| SAMPLE No. | POLYCHROMATOR OFFSET TIME | LIGHT SOURCE OFFSET TIME |
|---|---|---|
| 1 | T1 | T1' |
| 2 | T2 | T2' |
| 3 | T3 | T3' |
| ⋮ | ⋮ | ⋮ |

FIG.9

| SAMPLE No. | MEASUREMENT RESULT |
|---|---|
| 1 | MEASUREMENT RESULT 1(1) |
| 2 | MEASUREMENT RESULT 2(1) |
| 3 | MEASUREMENT RESULT 3(1) |
| ⋮ | ⋮ |

326

OPTICAL MEASUREMENT APPARATUS AND OPTICAL MEASUREMENT METHOD

TECHNICAL FIELD

The present invention relates to an optical measurement apparatus and an optical measurement method for measuring optical characteristics of one or a plurality of samples arranged on a rotary body.

BACKGROUND ART

A process for forming a film (mostly a thin film) on a base such as resin film or semiconductor substrate using any film deposition process is known. A method has been proposed for measuring characteristic values, such as film thickness, of a material produced by means of such a film deposition technique. For example, Japanese Patent Laying-Open No. 2013-019854 (PTD 1) discloses a method for measuring the thickness of a thin film in a measurement chamber in which the humidity is adjusted to be lower than the humidity of the outside, by connecting an oscillator to a detection unit and oscillating the oscillator in the measurement chamber.

A technique for optically measuring characteristics of a material produced by means of a film deposition technique as described above is also known. An optical measurement scheme can be employed to measure not only the film thickness but also a variety of optical characteristic values such as transmittance/reflectance, extinction coefficient, and refractive index.

CITATION LIST

Patent Document

PTD 1: Japanese Patent Laying-Open No. 2013-019854

SUMMARY OF INVENTION

Technical Problem

A film deposition process, which is one of the film deposition techniques, is a process in which one or a plurality of workpieces (hereinafter also referred to as "sample(s)") are arranged on the outer circumferential surface or rotary plane of a rotary body and a film is grown thereon while the rotary body is rotated. In the case of conventional measurement methods, optical characteristics of a sample in such a film deposition process could not be measured in real time. Therefore, there is a demand for an optical measurement apparatus and an optical measurement method with which optical characteristics of one or a plurality of samples arranged on a rotary body can be measured in situ.

Solution to Problem

According to an aspect of the present invention, an optical measurement apparatus for measuring an optical characteristic of one or a plurality of samples arranged on a rotary body is provided. The optical measurement apparatus includes a light source, a first detection unit configured to output a characteristic value of received light, a second detection unit having a higher response speed than the first detection unit and configured to output an intensity of received light, and a controller. The controller is configured to: cause, in a condition that a rotational speed of the rotary body is controlled so that the rotational speed is a specified value, the light source to generate light having a constant intensity and apply the light to an irradiation region which is a region where the samples pass as the rotary body rotates; and acquire first timing information based on a change with time of an intensity of reflected light or transmitted light that is output from the second detection unit receiving the reflected light or transmitted light of the applied light. Here, the first timing information is used for defining a period of time for which measurement by the first detection unit is enabled in association with a position of each sample. The controller is configured to: cause, in a condition that the rotational speed of the rotary body is controlled so that the rotational speed is the specified value, the light source to periodically generate pulsed light in accordance with the first timing information and apply the pulsed light to the irradiation region; and acquire second timing information based on a result which is output from the first detection unit as a result of measurement by the first detection unit periodically enabled in accordance with the first timing information. Here, the second timing information is used for defining a period of time for which the light source generates the pulsed light. The controller periodically enables, in a condition that the rotational speed of the rotary body is controlled so that the rotational speed is the specified value, measurement by the first detection unit in accordance with the first timing information and causes the light source to periodically generate pulsed light in accordance with the second timing information, to thereby acquire, for each sample, a characteristic value which is output from the first detection unit.

Preferably, the controller determines the first timing information from a position of the rotary body where the intensity which is output from the second detection unit has a maximum value or a minimum value.

More preferably, the controller causes the light generated by the light source and having a constant intensity to be applied to the irradiation region and causes the reflected light or the transmitted light of the applied light to be received by the second detection unit and further by the first detection unit, and corrects the first timing information based on a time deviation between an output from the first detection unit for a sample and an output from the second detection unit for the sample.

Preferably, the controller causes the light source to generate the pulsed light at multiple different timings, and determines, as the second timing information, a timing at which the output from the first detection unit is relatively larger.

Preferably, the apparatus further includes a position detection unit configured to detect a predetermined position of the rotary body that serves as a reference for defining the first timing information and the second timing information.

More preferably, the first timing information and the second timing information are defined using a time elapsed from detection of the predetermined position of the rotary body in a condition that the rotational speed of the rotary body is controlled so that the rotational speed is the specified value.

Preferably, the optical measurement apparatus further includes: a first group of optical fibers having respective end faces arranged along an axial direction of the rotary body and optically connected to the light source; and a second group of optical fibers having respective end faces arranged along the axial direction of the rotary body and optically connected to the first detection unit or the second detection unit.

According to another aspect of the present invention, an optical measurement method of measuring, with a detection unit, an optical characteristic of one or a plurality of samples arranged on a rotary body is provided. The optical measurement method includes the steps of:

causing, in a condition that a rotational speed of the rotary body is controlled so that the rotational speed is a specified value, a light source to generate light having a constant intensity and apply the light to an irradiation region which is a region where the samples pass as the rotary body rotates, and acquiring first timing information based on a change with time of an intensity of reflected light or transmitted light of the applied light;

causing, in a condition that the rotational speed of the rotary body is controlled so that the rotational speed is the specified value, the light source to periodically generate pulsed light in accordance with the first timing information and apply the pulsed light to the irradiation region, and acquiring second timing information based on a result which is output from the detection unit as a result of measurement by the detection unit periodically enabled in accordance with the first timing information; and periodically enabling, in a condition that the rotational speed of the rotary body is controlled so that the rotational speed is the specified value, measurement by the detection unit in accordance with the first timing information and causing the light source to periodically generate pulsed light in accordance with the second timing information, to thereby acquire, for each sample, a characteristic value which is output from the detection unit.

Advantageous Effects of Invention

According to the present invention, optical characteristics of one or a plurality of samples arranged on a rotary body can be measured in situ.

BRIEF DESCRIPTION OF DRAWINGS

FIG. 7 is a diagram showing an example of timing information acquired through pre-measurement of the first measurement method according to the present embodiment.

FIG. 9 is a diagram showing an example of the results of measurement acquired through the primary measurement of the first measurement method according to the present embodiment.

DESCRIPTION OF EMBODIMENTS

Figure 1:
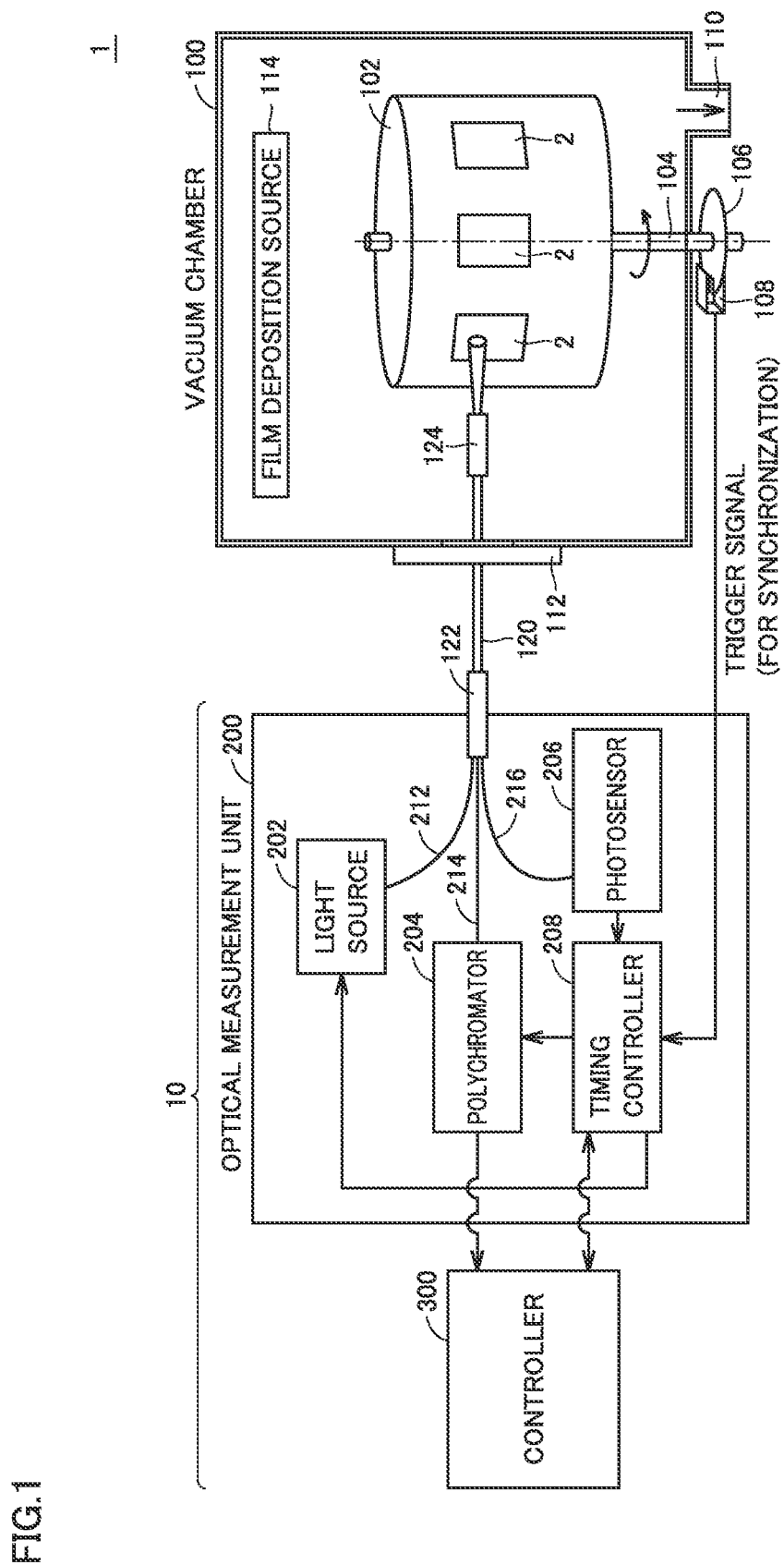
FIG. 1 is a schematic diagram showing a configuration of a film deposition system including an optical measurement apparatus according to the present embodiment.

An embodiment of the present invention will be described in detail with reference to the drawings. It should be noted that the same or corresponding parts in the drawings are denoted by the same reference characters, and a description thereof will not be repeated.

<A. Apparatus Configuration of Film Deposition System>

First, a description will be given of an apparatus configuration of a film deposition system including an optical measurement apparatus according to the present embodiment. FIG. 1 is a schematic diagram showing a configuration of a film deposition system 1 including an optical measurement apparatus 10 according to the present embodiment. Referring to FIG. 1, film deposition system 1 implements a process for forming a film on a sample 2 in a vacuum environment. Film deposition system 1 includes optical measurement apparatus 10 and a vacuum chamber 100.

In vacuum chamber 100, a rotary drum 102 which is a rotary body rotatably driven by a drive mechanism (not shown) is arranged. On the side surface of rotary drum 102, one or a plurality of samples 2 are arranged. Samples 2 may be arranged regularly or may be arranged irregularly. Before a film deposition process is started, the air present inside vacuum chamber 100 is discharged from a suction opening 110 and the vacuum chamber is kept in a state (vacuum state in an industrial sense) of being filled with gas having a lower pressure than the atmospheric pressure (the pressure outside vacuum chamber 100). In this state, rotary drum 102 is rotated at a predetermined constant rotational speed (specified rotational speed/specified number of revolutions) while substances which are to form the material for the film are released from a film deposition source 114. For example, the specified rotational speed may be 50 to 200 [rpm] for example. On a surface of sample 2, a chemical reaction with substances released from film deposition source 114 is caused by electrons, ions, plasma, light, or the like, and this chemical reaction causes a film to be formed on sample 2.

On the axis of a rotational shaft 104 of rotary drum 102, a rotary plate 106 is integrally placed. A rotation detection sensor 108 is arranged in parallel with the rotary surface of rotary plate 106. Rotation detection sensor 108 detects the rotational position (angle) of rotary plate 106 which is rotated as rotary drum 102 is rotated. On the surface of rotary plate 106, a predetermined pattern is formed. Rotation detection sensor 108 detects the predetermined pattern to thereby output an absolute or relative rotational position of rotary drum 102.

In the present embodiment, it is at least necessary to acquire the timing at which rotary drum 102 reaches a rotational position serving as a certain reference, as will be described later herein. Thus, at the timing when rotary drum 102 reaches the rotational position serving as the reference, a trigger signal is output. The trigger signal is a signal indicating that a reference point or home position is detected. This trigger signal is used as a signal (synchronization signal) for synchronizing measurement in optical measurement apparatus 10. Namely, rotation detection sensor 108 corresponds to a position detection unit for detecting a predetermined position of rotary drum 102 (rotary body) that serves as a reference for defining each timing included in timing information 324.

While FIG. 1 chiefly shows, by way of example, the configuration for forming a film on a sample by a vacuum vapor deposition process, the film deposition process is not limited to this. This is applicable for example to monitoring or control of a process for forming a thin film on a base film by the sputtering method, a process for bonding a plurality of films together, or the like.

Optical measurement apparatus 10 measures optical characteristics of sample 2 in the course of formation of a film on sample 2 in vacuum chamber 100. Sample 2 corresponds to an object to be measured by the optical measurement method according to the present embodiment.

Optical measurement apparatus 10 includes an optical measurement unit 200 and a controller 300. Optical measurement unit 200 generates light to be applied to sample 2, receives light reflected from sample 2 or transmitted through sample 2, and measures an optical characteristic of sample 2. Controller 300 controls generation and application of light by optical measurement unit 200 as well as detection of light from sample 2, for example.

Vacuum chamber 100 and optical measurement unit 200 are optically connected through a bundle fiber 120 corresponding to a light guide unit. Bundle fiber 120 extends through a window 112 of vacuum chamber 100 and partially arranged in vacuum chamber 100. A fiber probe 124 provided on one end of bundle fiber 120 is arranged in vacuum chamber 100. Meanwhile, a fiber probe 122 provided on the other end of bundle fiber 120 is arranged in association with optical measurement unit 200.

Optical measurement unit 200 includes a light source 202, a polychromator 204, a photosensor 206, and a timing controller 208. Light source 202, polychromator 204, and photosensor 206 are optically connected to fiber probe 122 through optical fibers 212, 214, and 216, respectively. The structure of bundle fiber 120 will be described later herein.

Light source 202 generates light (hereinafter also referred to as "incident light") to be applied to sample 2. The incident light generated by light source 202 is applied through optical fiber 212 and bundle fiber 120 to the side surface of rotary drum 102. In the present embodiment, the timing at which the incident light is applied is made appropriate for directing the incident light to each of samples 2 arranged on the side surface. Light source 202 is configured so that one of its operation of generating incident light continuously and its operation of generating incident light in a pulsed manner can be selected. In the case where pulsed incident light is generated, the intensity of incident light generated by light source 202 is varied with time in accordance with a command from timing controller 208.

The type (wavelength) of light to be generated by light source 202 is appropriately selected depending on a material for sample 2 and a material for a film formed on sample 2. For example, light in any one or more than one of the visible range (360 nm-830 nm), the near-ultraviolet range (200 nm-360 nm), and the near-infrared range (830 nm-2000 nm) is used.

Polychromator 204 corresponds to a detection unit which receives light reflected from (or light transmitted through) sample 2 and outputs a characteristic value of the received light. Polychromator 204 is a kind of spectrometer, receives light reflected from (or light transmitted through) sample 2, and outputs the intensity of each wavelength (spectrum) included in the received light. In other words, although an example where the spectrum is measured as a characteristic value of light is illustrated, the characteristic value is not limited to the spectrum and a detection unit capable of measuring any characteristic value (such as refractive index, reflectance, extinction coefficient, for example) can be used. In the case where the spectrum is measured, a spectroscopic ellipsometer or the like, for example, may be used instead of the polychromator.

Photosensor 206 is a photoreceiver chiefly for acquiring timing information as will be described later herein, receives light reflected from (or light transmitted through) sample 2, and outputs the intensity of the received light. Photosensor 206 is typically formed of a photodiode or photodetector. Since photosensor 206 is chiefly used for detecting the timing which depends on the position where sample 2 is arranged, photosensor 206 preferably has a higher response speed than polychromator 204. Namely, it is preferable that, in the case where photosensor 206 and polychromator 204 receive light at the same timing, the result is output from photosensor 206 before the result is output from polychromator 204. Ideally, upon receiving light reflected from (or light transmitted through) sample 2, photosensor 206 substantially instantaneously outputs the intensity of the received light.

Timing controller 208 controls the operation timing of each of light source 202 and polychromator 204 in accordance with the trigger signal from rotation detection sensor 108, the result of detection from photosensor 206, and a command from controller 300, for example. More specifically, based on timing information acquired in advance, timing controller 208 controls the timing when (or period of time for which) light source 202 generates (applies) the incident light, and also controls the timing when (or period of time for which) measurement by polychromator 204 is enabled.

Controller 300 controls the operation of optical measurement unit 200 and stores optical characteristic values measured by optical measurement unit 200. Controller 300 has a user interface for accepting operation by a user, and a user interface for presenting measured optical characteristic values to a user, for example.

<B. Apparatus Configuration of Controller>

Next, an apparatus configuration of controller 300 will be described. Controller 300 can typically be implemented using a general-purpose computer.

Figure 2:
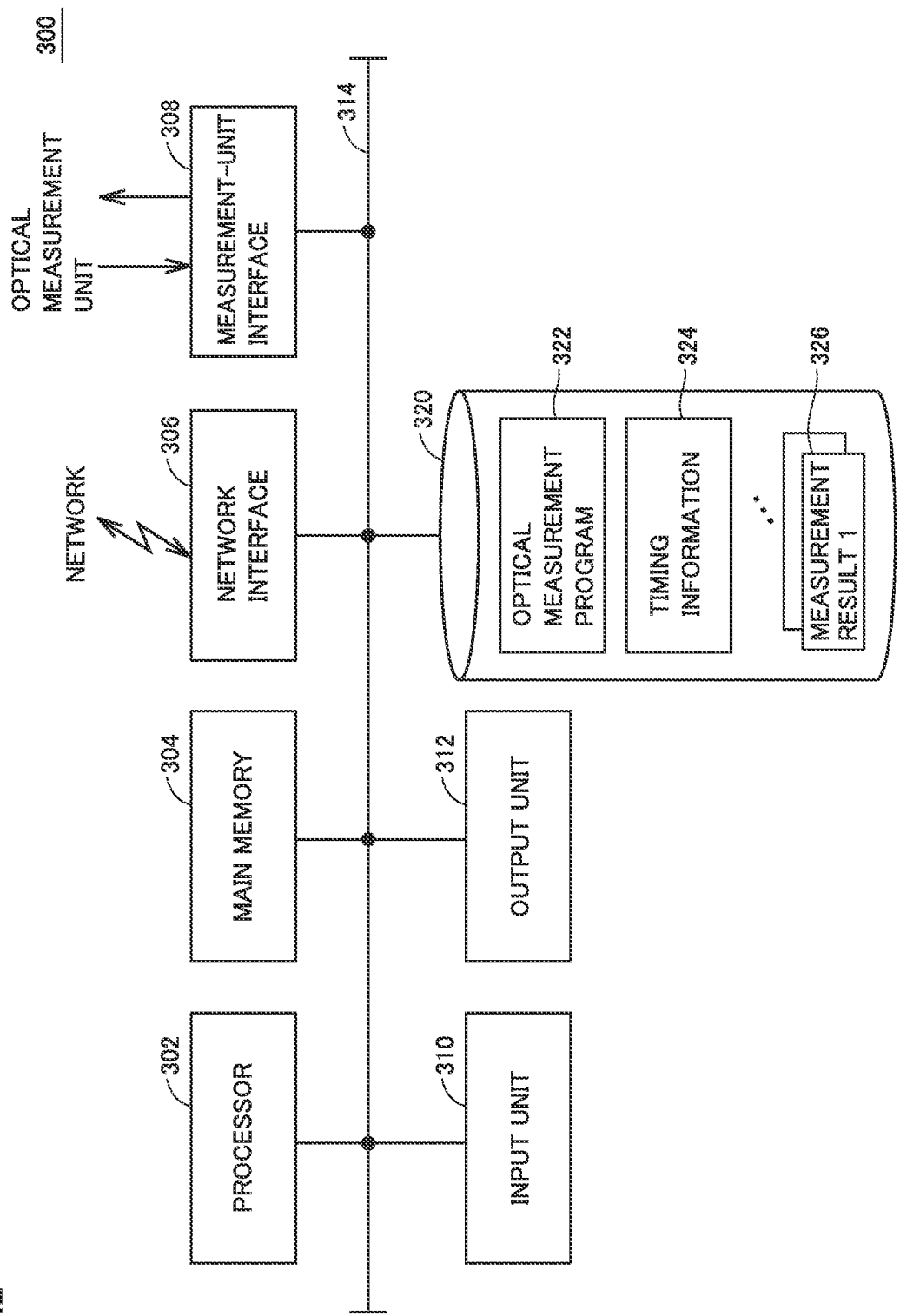
FIG. 2 is a schematic diagram showing a configuration of a controller which is a component of the optical measurement apparatus according to the present embodiment.

FIG. 2 is a schematic diagram showing a configuration of controller 300 which is a component of optical measurement apparatus 10 according to the present embodiment. Referring to FIG. 2, controller 300 includes a processor 302 executing various programs including operating system (OS), a main memory 304 temporarily storing data necessary for execution of programs by processor 302, and a hard disk 320 storing, in a non-volatile manner, programs executed by processor 302 as well as data. Processor 302 receives instructions from a user for example via an input unit 310 composed of a keyboard, a mouse, or the like, and presents to a user various user interface screens via an output unit 312 composed of a display or the like.

Controller 300 further includes a network interface 306 and a measurement-unit interface 308. Network interface 306 exchanges data with an external device or the like (not shown) on a network. A program or the like which is downloaded via network interface 306 is installed in hard disk 320 of controller 300, or a result of measurement or the like acquired by controller 300 is transmitted via network interface 306 to an external device. Measurement-unit interface 308 exchanges data with optical measurement unit 200. More specifically, measurement-unit interface 308 acquires the result of measurement by polychromator 204 (FIG. 1) and provides generated timing information to timing controller 208 (FIG. 1).

The components constituting controller 300 are connected via a bus 314 so that they can communicate data to each other.

Hard disk 320 stores an optical measurement program 322, timing information 324, a measurement result 326, and the like. Optical measurement program 322 is executed by processor 302 to implement various processes involved in an optical measurement method described later herein. Optical measurement program 322 may be downloaded from a server apparatus or the like via network interface 306, or optical measurement program 322 stored in any recording medium such as optical disk may be read and installed. Timing information 324 controls the timing when (or period of time for which) light source 202 of optical measurement unit 200 generates (applies) incident light, and controls the timing when (or period of time for which) measurement by polychromator 204 is enabled. Measurement result 326 includes a measurement value acquired from polychromator 204 for example.

<C. Overview of Optical Measurement Method>

Conventionally, in a film deposition process in a vacuum chamber, it has been impossible to perform in-situ measurement of a sample arranged on a rotary body during the film deposition. It has only been possible to perform in-situ measurement of a test piece arranged in a stationary manner in a vacuum chamber, not the sample arranged on the rotary body. Therefore, optical characteristics of a sample to be measured arranged on the rotary body could only be measured after completion of the film deposition process. It has been impossible to monitor in real time the progress of the film deposition process.

Even when the test piece and the sample to be measured are arranged in the same vacuum chamber, respective environments for example in which the test piece and the sample to be measured are arranged differ from each other, and therefore, respective film deposition processes that actually occur also differ from each other and a measured optical characteristic of the test piece do not accurately reflect the optical characteristic of the sample to be measured.

In contrast, regarding the optical measurement method of the present embodiment, an optical characteristic of one or a plurality of samples arranged on a rotary body (typically a rotary drum or rotary stage) and varying in position with time is measured sample by sample. The timing which is determined in accordance with the speed of movement of sample 2 and a time frame for which moving sample 2 is in a measurable range is acquired in advance and, in accordance with the acquired timing, the timing when (or period for which) light source 202 generates (applies) incident light or the timing when (or period for which) measurement by polychromator 204 is enabled are controlled to perform in-situ measurement of an optical characteristic of each sample 2.

According to the optical measurement method in the present embodiment, a synchronization timing is set in accordance with the position where each sample is arranged. Therefore, measurement can be performed even when samples are irregularly arranged. Further, measurement with high precision is possible even when the rotational speed of the rotary body varies.

Since an optical characteristic of each sample 2 can be measured in situ, progress of a film deposition process for each sample can be monitored in real time.

<D. First Measurement Method>

Next, a description will be given of a first measurement method according to the present embodiment. The first measurement method includes two kinds of measurement procedures: preliminary measurement for acquiring timing information 324 which depends on the position where sample 2 is arranged on rotary drum 102 (hereinafter also referred to as "pre-measurement"); and primary measurement for acquiring an optical characteristic of each sample 2 (hereinafter also referred to as "primary measurement"). Further, the pre-measurement includes two stages of measurement procedures (hereinafter also referred to as "pre-measurement (1)" and "pre-measurement (2)"). By the pre-measurement, the timing when light source 202 applies pulsed incident light and the timing when measurement by polychromator 204 is enabled are determined.

Figure 3:
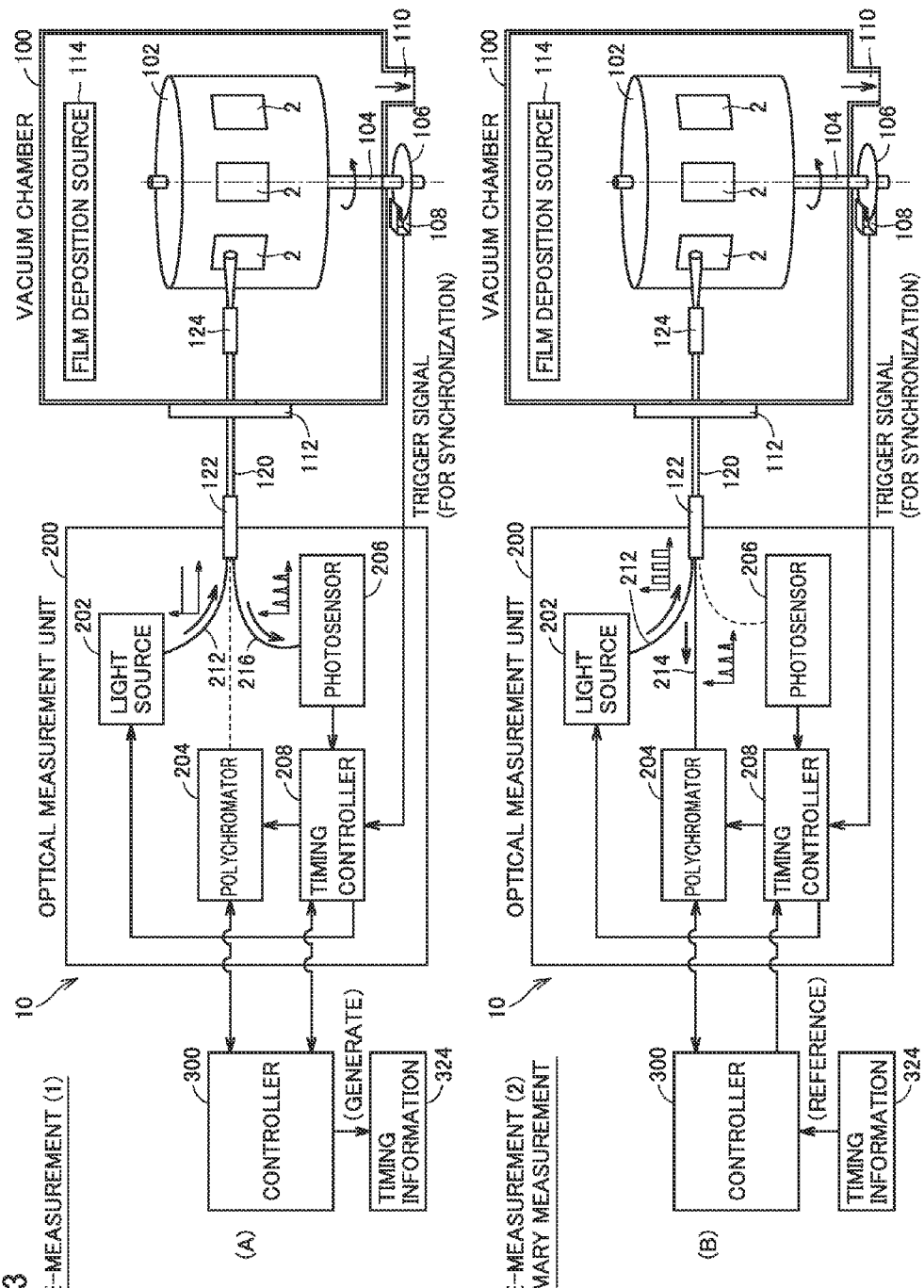
FIG. 3 is a schematic diagram for illustrating a first measurement method according to the present embodiment.

FIG. 3 is a schematic diagram for illustrating the first measurement method according to the present embodiment. In FIG. 3 (A), a relation of connection for the pre-measurement (1) is shown. In FIG. 3 (B), a relation of connection for the pre-measurement (2) and the primary measurement is shown.

<<d1: Pre-Measurement (1)>>

First, the pre-measurement (1) is performed. By the pre-measurement (1), a timing table for driving polychromator 204 in a synchronized manner that is associated with the position where each sample 2 is arranged is generated as a part of timing information 324.

Referring to FIG. 3 (A), when the pre-measurement (1) is performed, continuous incident light is generated from light source 202, the continuously generated incident light is reflected from the side surface of rotary drum 102, and the intensity of the resultant light is detected by photosensor 206. Light source 202 is optically connected through optical fiber 212 to vacuum chamber 100, and photosensor 206 is optically connected through optical fiber 216 to vacuum chamber 100.

When the pre-measurement (1) is performed, rotary drum 102 is kept at a specified rotational speed, as done when the primary measurement is performed. Therefore, the intensity of the reflected light detected by photosensor 206 varies with time depending on the position of sample 2 arranged on the side surface of rotary drum 102. Based on the variation with time of the intensity of the reflected light, the timing table indicating the position of sample 2 arranged on rotary drum 102 is generated. Since rotary drum 102 is rotating, the position of sample 2 is defined as a relative distance (time) from a predetermined position (reference point/home position) of rotary drum 102. In the configuration shown in FIG.

3, the trigger signal which is output from rotation detection sensor 108 is used as a reference point.

Figure 4:
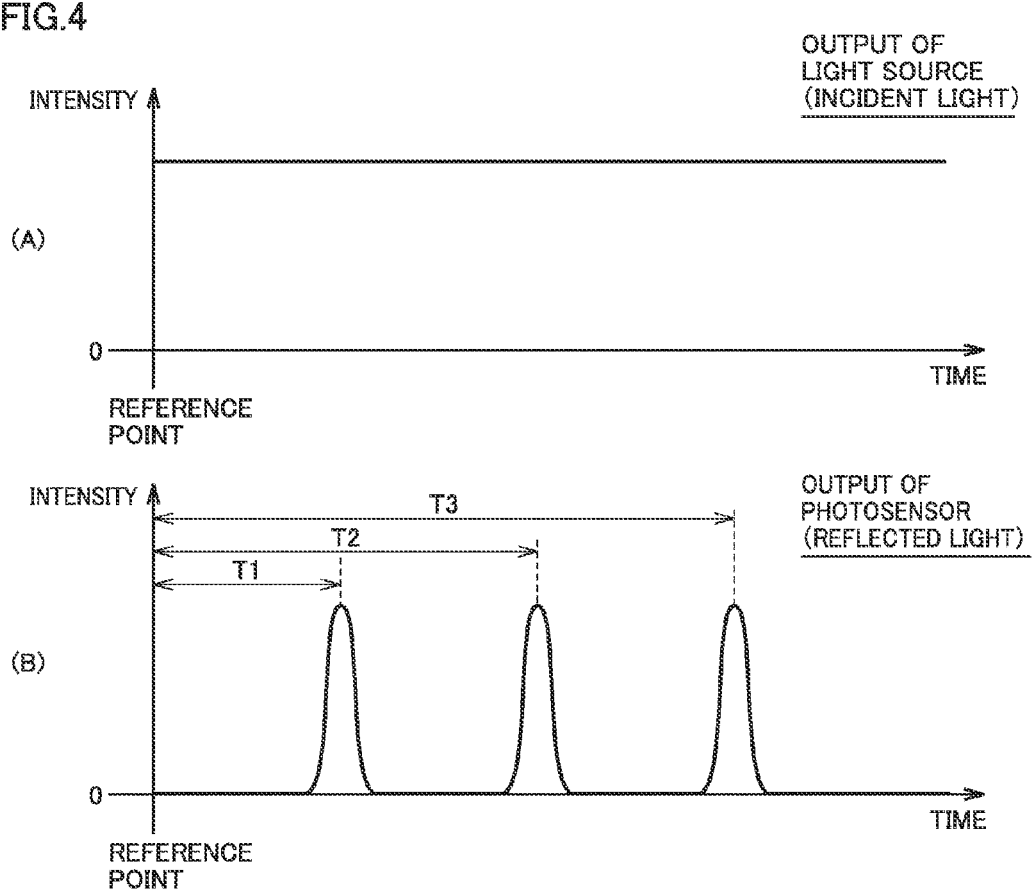
FIG. 4 is a diagram showing a time waveform of each part when pre-measurement (1) of the first measurement method is performed according to the present embodiment.

FIG. 4 is a diagram showing a time waveform of each part when the pre-measurement (1) of the first measurement method is performed according to the present embodiment. In FIG. 4 (A), a time waveform of incident light generated by light source 202 is shown. In FIG. 4 (B), a time waveform of reflected light which is output by photosensor 206 is shown.

As shown in FIG. 4 (A), the incident light of a constant intensity is applied from light source 202, this incident light is reflected from sample 2, and accordingly the reflected light whose intensity varies with time as shown in FIG. 4 (B) is generated. Timing information 324 includes information about the position of each point which provides the maximum intensity of the reflected light. More specifically, offset time T1, T2, T3, . . . is acquired which is a relative time difference of each point providing the maximum intensity, from the reference point. Thus, from the position of rotary drum 102 where photosensor 206 outputs an intensity of the maximum value or the minimum value, offset time T1, T2, T3, . . . (first timing information) is determined.

Offset time T1, T2, T3, . . . derived from the result of output of photosensor 206 is used as a synchronization timing at which measurement by polychromator 204 is enabled. This makes use of the fact that both polychromator 204 and photosensor 206 apply incident light toward sample 2 through common fiber probe 124, namely the commonness of the optical path.

In this way, the position (time) of rotary drum 102 where photosensor 206 outputs the maximum value, with respect to the reference point of rotary drum 102, is examined and recorded for each sample 2, to thereby generate the timing table associated with the position where each sample 2 is arranged, for driving polychromator 204 in a synchronized manner.

As seen from the foregoing, in a condition that the rotational speed of rotary drum 102 is controlled so that the rotational speed is a specified value, the incident light of a constant intensity generated by light source 202 is applied to an irradiation region which is a region where sample 2 passes as rotary drum 102 rotates. The reflected light (or transmitted light as will be described later herein) of the applied incident light is received by photosensor 206. Based on variation with time of the intensity which is accordingly output from photosensor 206 (see FIG. 4 (B)), offset time T1, T2, T3, . . . (first timing information) is acquired. This offset time T1, T2, T3, . . . is used for defining a period of time for which measurement by polychromator 204 is enabled in association with the position of each sample 2.

In the case of actual pre-measurement (1), the timing table is generated from the results of measurement performed over a certain period of time. Namely, multiple sets of offset time T1, T2, T3, . . . shown in FIG. 4 (B) are acquired and each offset time undergoes statistical processing to thereby determine final offset time T1, T2, T3, . . . . The statistical processing may be simple averaging processing or processing for which standard deviation (variance) is taken into consideration.

<<d2: Pre-Measurement (2)>>

Subsequently, the pre-measurement (2) is performed. By the pre-measurement (2), a deviation of time (delay time) between the timing for driving polychromator 204 in a synchronized manner and the timing when pulsed incident light is generated from light source 202 is calculated as a part of timing information 324. From the calculated delay time, a timing table which is associated with the position where each sample 2 is arranged and used for driving light source 202 in a synchronized manner is generated.

Referring to FIG. 3 (B), when the pre-measurement (2) is performed, pulsed incident light is generated from light source 202, and the pulsed incident light is reflected from sample 2 arranged on the side surface of rotary drum 102, and the resultant light is received by polychromator 204. Light source 202 is optically connected through optical fiber 212 to vacuum chamber 100, and polychromator 204 is optically connected through optical fiber 214 to vacuum chamber 100.

When the pre-measurement (2) is performed, rotary drum 102 is kept at a specified rotational speed, as done when the pre-measurement (1) and the primary measurement are performed. In this condition, measurement by polychromator 204 is enabled in accordance with offset time T1, T2, T3, . . . (synchronization timing of polychromator 204) determined by the pre-measurement (1) and, the timing of the pulsed incident light at which most efficient measurement is possible at this time is determined. Namely, while polychromator 204 is driven in accordance with the synchronization timing determined by the pre-measurement (1), the timing when the pulsed incident light is applied from light source 202 is changed. Based on the results of output of polychromator 204 obtained in this case, the synchronization timing when light source 202 is driven is determined.

While the synchronization timing of light source 202 may be determined for each sample 2 arranged on the side surface of rotary drum 102, the following description is of a process example for determining the synchronization timing of light source 202, based on one sample 2 (typically sample 2 arranged at the position closest to the reference point of rotary drum 102).

Figure 5:
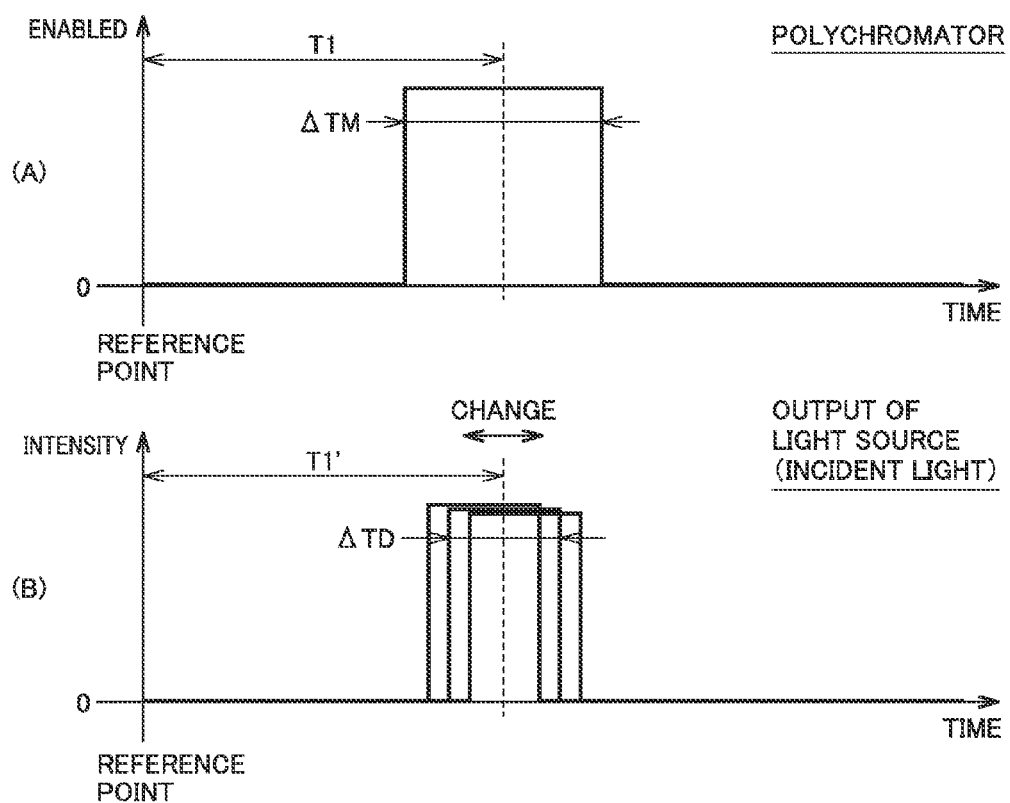
FIG. 5 is a diagram for illustrating details of adjustments made by pre-measurement (2) of the first measurement method according to the present embodiment.

FIG. 5 is a diagram for illustrating details of adjustments made by the pre-measurement (2) of the first measurement method according to the present embodiment.

In FIG. 5 (A), the timing when measurement by polychromator 204 is enabled is shown. In FIG. 5 (B), the timing when the pulsed incident light generated by light source 202 is applied is shown. As shown in FIG. 5 (A), measurement by polychromator 204 is enabled for a predetermined time width $\Delta TM$. For sample 2 (first sample) arranged at the position closest to the reference point of rotary drum 102, the measurement is enabled for time width $\Delta TM$ centered at offset time T1. As shown in FIG. 5 (B), light source 202 generates pulsed light having a predetermined time width $\Delta TD$ as the incident light.

Time width $\Delta TD$ of the pulsed light generated by light source 202 is designed in advance based on the specified rotational speed of rotary drum 102, the size of sample 2, and the distance between samples 2 adjacent to each other, for example. Time width $\Delta TM$ for which polychromator 204 is enabled is designed in advance based on the response speed of polychromator 204 and time width $\Delta TD$ of the pulsed light, for example.

As shown in FIG. 5 (B), the timing when light source 202 applies the pulsed light (offset time T1' from the reference point) is changed to search for a timing at which the output of polychromator 204 is the maximum output. Namely, while the period for which light source 202 applies the pulsed light is kept in the period of the synchronization timing of polychromator 204, the phase in which light source 202 applies the pulsed light is successively changed to search for the optimum timing (phase difference).

Figure 6:
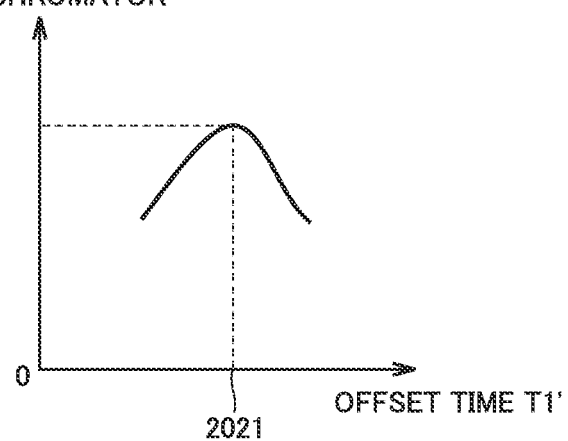
FIG. 6 is a diagram for illustrating the result of adjustments made by pre-measurement (2) of the first measurement method according to the present embodiment.

FIG. 6 is a diagram for illustrating the result of adjustments made by the pre-measurement (2) of the first measurement method according to the present embodiment.

Referring to FIG. 6, the result of adjustments of the timing when light source 202 applies the pulsed light (delay time from the reference point to the center of the pulsed light (offset time T1')) is shown. As shown in FIG. 6, offset time T1' at which the result of output (detection sensitivity) of polychromator 204 is the maximum output (reference numeral 2021) is determined.

Further, from offset time T1' of light source 202 which is determined for sample 2 (first sample) arranged at the position closest to the reference point of rotary drum 102, offset time T2', T3', . . . of light source 202 for remaining samples 2 is calculated. More specifically, the difference between offset time T1 and offset time T1' (=T1−T1') for sample 2 (first sample) arranged at the position closest to the reference position of rotary drum 102 is reflected on other offset time T2, T3, . . . to thereby determine offset time T2', T3', . . . of light source 202.

Thus, the timing when light source 202 generates the pulsed light is set to multiple different timings and a timing at which the output of polychromator 204 is relatively larger is determined as offset time T2', T3', . . . (second timing information).

As seen from the foregoing, in a condition that the rotational speed of rotary drum 102 is controlled so that the rotational speed is a specified value, the pulsed incident light periodically generated by light source 202 in accordance with offset time T1, T2, T3, . . . (first timing information) is applied to an irradiation region which is a region where sample 2 passes as rotary drum 102 rotates. Then, based on the result of output of polychromator 204 whose measurement is periodically enabled in accordance with offset time T1, T2, T3, . . . (first timing information), offset time T1', T2', T3', . . . (second timing information) is acquired. This offset time T1', T2', T3', . . . is used for defining the period for which the pulsed light is generated from light source 202.

Ideally, the synchronization timing (offset time T1, T2, T3, . . . ) of polychromator 204 matches the synchronization timing (offset time T1', T2', T3, . . . ) of light source 202. However, due to the influences of the fact that sample 2 is rotating, the response delay from receipt of a command to generation of light by light source 202, and the response delay from enablement to stabilization of measurement by polychromator 204, for example, these timings do not match in most cases.

Through the above-described pre-measurement (1) and pre-measurement (2), timing information 324 is acquired. It should be noted that in the case where the synchronization timing of polychromator 204 can be considered as matching the synchronization timing of light source 202, the above-described pre-measurement (2) may be skipped. In this case, the synchronization timing of light source 202 is also determined based on the result of the pre-measurement (1). Namely, timing information 324 may be determined through the pre-measurement (1) only.

FIG. 7 is a diagram showing an example of timing information 324 acquired through the pre-measurement of the first measurement method according to the present embodiment. As shown in FIG. 7, timing information 324 includes synchronization timings associated with each sample number which is provided for identifying sample 2 arranged on rotary drum 102. The synchronization timings include offset time T1, T2, T3, . . . which is the synchronization timing of polychromator 204 and offset time T1', T2', T3', . . . which is the synchronization timing of light source 202. Offset time T1, T2, T3, . . . (first timing information) and offset time T1', T2', T3', . . . (second timing information) are defined using the time elapsed from detection of a predetermined position (reference point/home position) of rotary drum 102 in a condition that the rotational speed of rotary drum 102 (rotary body) is controlled so that the speed is a specified value.

<<d3: Primary Measurement>>

Using timing information 324 acquired through the above-described pre-measurement, the primary measurement is performed. It should be noted that the pre-measurement may not necessarily be performed before the primary measurement. For example, in such a case where the same film deposition process is repeated for samples 2 in the same lot, the pre-measurement may be performed only once and timing information 324 acquired from the pre-measurement may commonly be used to perform the primary measurement multiple times.

Referring again to FIG. 3 (B), when the primary measurement is performed, pulsed incident light is generated from light source 202 as done in the above-described pre-measurement (2), the pulsed incident light is reflected from sample 2 arranged on the side surface of rotary drum 102, and the resultant light is received by polychromator 204. Light source 202 is optically connected through optical fiber 212 to vacuum chamber 100, and polychromator 204 is optically connected through optical fiber 214 to vacuum chamber 100.

When the primary measurement is done, the timing when light source 202 applies the pulsed light is controlled based on timing information 324 so that the incident light is applied to sample 2 only. By appropriate control of the timing when the incident light is applied, polychromator 204 can selectively receive only the light reflected from each sample 2.

Figure 8:
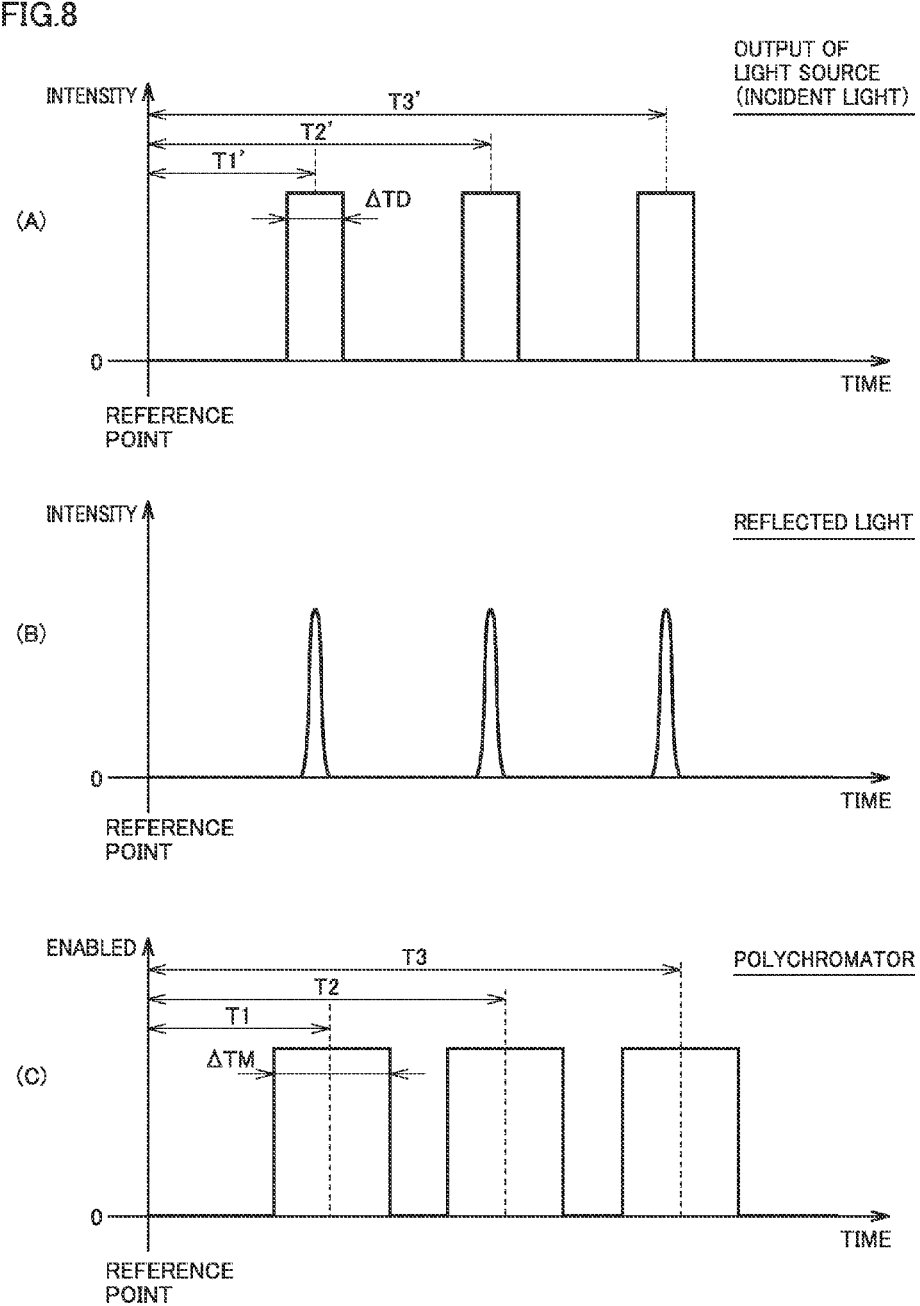
FIG. 8 is a diagram showing a time waveform of each part when primary measurement of the first measurement method is performed according to the present embodiment.

FIG. 8 is a diagram showing a time waveform of each part when the primary measurement of the first measurement method is performed according to the present embodiment. In FIG. 8 (A), a time waveform of the incident light generated by light source 202 is shown. In FIG. 8 (B), a time waveform of the reflected light which enters polychromator 204 is shown. In FIG. 8 (C), the timing when polychromator 204 is enabled is shown.

Referring to FIG. 8 (A), when the primary measurement is done, the pulsed incident light is generated from light source 202 with reference to timing information 324 acquired through the pre-measurement. Light source 202 generates the pulsed light having predetermined time width ΔTD centered at each offset time T1', T2', T3', . . . which is the synchronization timing.

The pulsed light generated by light source 202 is reflected from each sample 2 arranged on rotary drum 102 and accordingly the pulsed reflected light as shown in FIG. 8 (B) is generated. The period of time for which measurement by polychromator 204 is enabled is controlled as shown in FIG. 8 (C) so that it corresponds to the pulsed incident light shown in FIG. 8 (A) and the pulsed reflected light shown in FIG. 8 (B). More specifically, measurement by polychromator 204 is enabled for predetermined time width ΔTM centered at each offset time T1, T2, T3, . . . which is the synchronization timing. Measurement by polychromator 204 can be periodically enabled to individually measure a plurality of rotating samples 2.

Thus, in a condition that the rotational speed of rotary drum 102 is controlled so that the rotational speed is a specified value, measurement by polychromator 204 is periodically enabled in accordance with offset time T1, T2, T3, . . . (first timing information). In addition, the pulsed light is periodically generated by light source 202 in accordance with offset time T1', T2', T3', . . . (second timing information). Through this synchronization process, a characteristic value which is output from polychromator 204 can be acquired for each sample 2.

FIG. 9 is a diagram showing an example of the results of measurement acquired through the primary measurement of the first measurement method according to the present embodiment. Referring to FIG. 9, for each sample 2 arranged on rotary drum 102, the result of measurement by polychromator 204 is stored. Typically, the condition of film deposition on sample 2 is measured in situ. Therefore, the results of measurement for respective samples 2 are successively stored each associated with a specific time.

<<d4: Process Procedure>>

Figure 10:
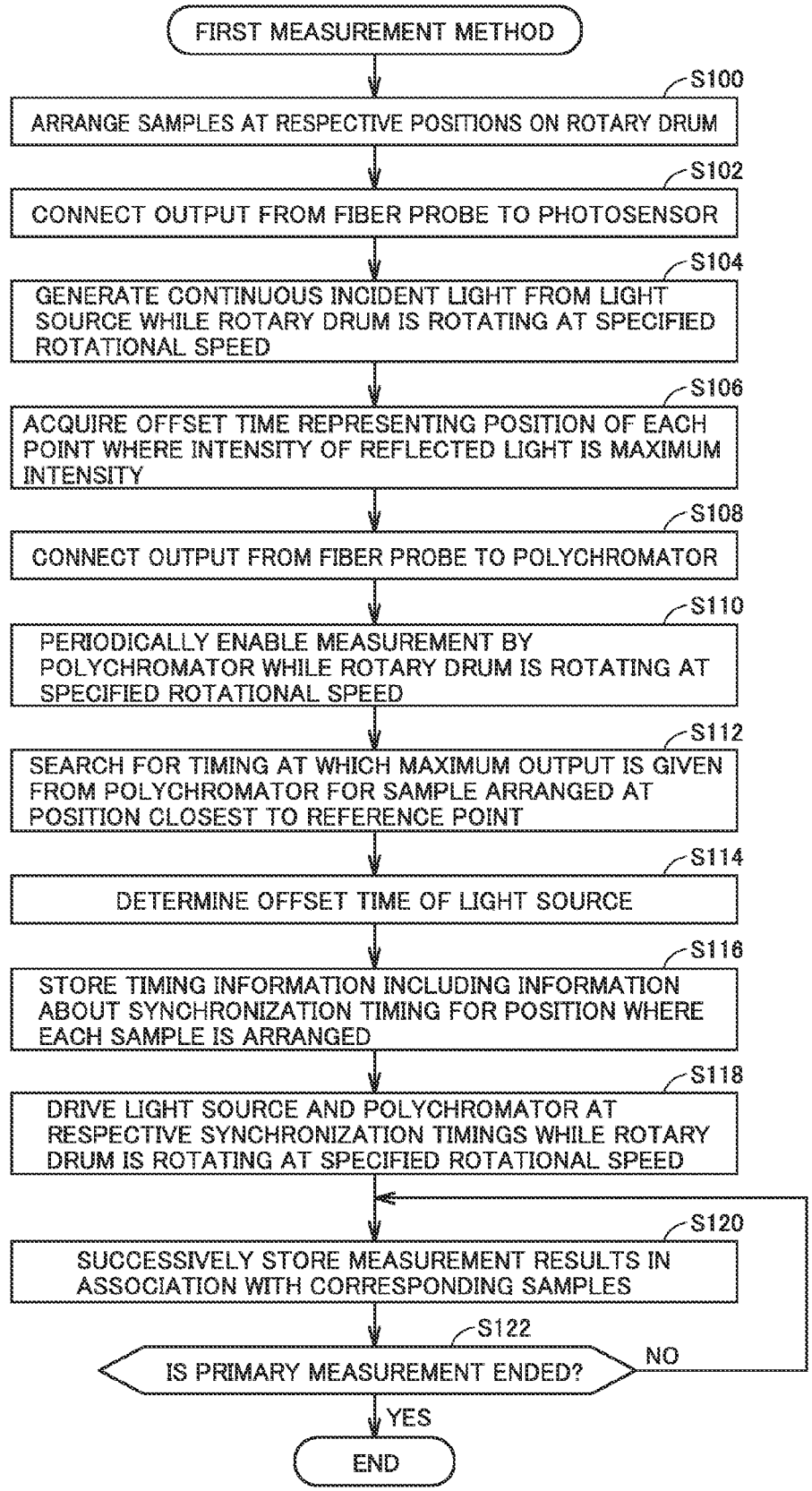
FIG. 10 is a flowchart showing a process procedure of the first measurement method according to the present embodiment.

FIG. 10 is a flowchart showing a process procedure of the first measurement method according to the present embodiment. Referring to FIG. 10, preparation for measurement is done first. More specifically, an operator arranges samples 2 (typically substrates on which films have not been deposited yet) at respective positions on rotary drum 102 (step S100). Subsequently, the operator connects an output from fiber probe 122 to photosensor 206 in optical measurement unit 200 (step S102). It should be noted that the operations in step S100 and S102 may be performed automatically by a dedicated apparatus or the like.

After this, an instruction to start the pre-measurement (1) is given. Then, in a condition that rotary drum 102 is rotating at a specified rotational speed which is the same condition as the primary measurement (namely the condition when a film deposition process is performed on sample 2), controller 300 causes light source 202 to generate continuous incident light (step S104). Controller 300 acquires offset time T1, T2, T3, . . . representing the position of each point which provides the maximum intensity of the reflected light received by photosensor 206 (step S106). Timing information 324 includes offset time T1, T2, T3, . . . . From acquired offset time T1, T2, T3, . . . , the synchronization timing of polychromator 204 is acquired, for the position where each sample 2 is arranged with respect to a reference point of rotary drum 102.

Subsequently, preparation for transition to the pre-measurement (2) is done. More specifically, the operator connects an output from fiber prove 122 to polychromator 204 in optical measurement unit 200 (step S108). It should be noted that the operation in step S108 may be performed automatically by a dedicated apparatus (such as a switching device for an optical path) or the like.

After this, an instruction to start the pre-measurement (2) is given. Then, in a condition that rotary drum 102 is rotating at a specified rotational speed which is the same condition as the primary measurement (namely the condition when a film deposition process is performed on sample 2), controller 300 periodically enables measurement by polychromator 204 in accordance with offset time T1, T2, T3, . . . acquired in step S106 (step S110). Then, controller 300 successively varies the timing (offset time T1' from the reference point) at which light source 202 applies the pulsed time to search for the timing at which the maximum output is given from polychromator 204 for sample 2 (first sample) arranged at the position closest to the reference point of rotary drum 102 (step S112). Namely, it searches for offset time T1' at which the maximum output is given from polychromator 204. Further, controller 300 calculates the difference between offset time T1 and offset time T1' at which the output from polychromator 204 is the maximum output, and allows the difference to be reflected on other offset time T2, T3, . . . to thereby determine offset time T1', T2', T3', . . . of light source 202 (step S114). Timing information 324 includes offset time T1', T2', T3', . . . .

From the acquired offset time T1', T2', T3', . . . , the relation of time between the synchronization timing of polychromator 204 and the synchronization timing at which light source 202 generates the incident light is acquired.

Finally, controller 300 stores timing information 324 including information about the synchronization timing, for the position where each sample 2 is arranged, with respect to the reference point of rotary drum 102 (step S116). Timing information 324 includes a time table for measuring each sample 2 in a synchronized manner. More specifically, timing information 324 includes information indicating the synchronization timing at which measurement by polychromator 204 is enabled as well as the synchronization timing at which light source 202 generates the pulsed incident light.

After this, an instruction to start the primary measurement is given. Then, in a condition that rotary drum 102 is rotating at a specified rotational speed, controller 300 drives light source 202 and polychromator 204 at respective synchronization timings, with reference to timing information 324 (step S118), and successively stores, in association with corresponding samples 2, the results of measurement which are output from polychromator 204 for respective samples 2 (step S120). This measurement process is repeated until an instruction to end the primary measurement is given (NO in step S122).

<<d5: Structure of Fiber Probe>>

Next, a structure of fiber probe 124 arranged in vacuum chamber 100 will be described.

Figure 11:
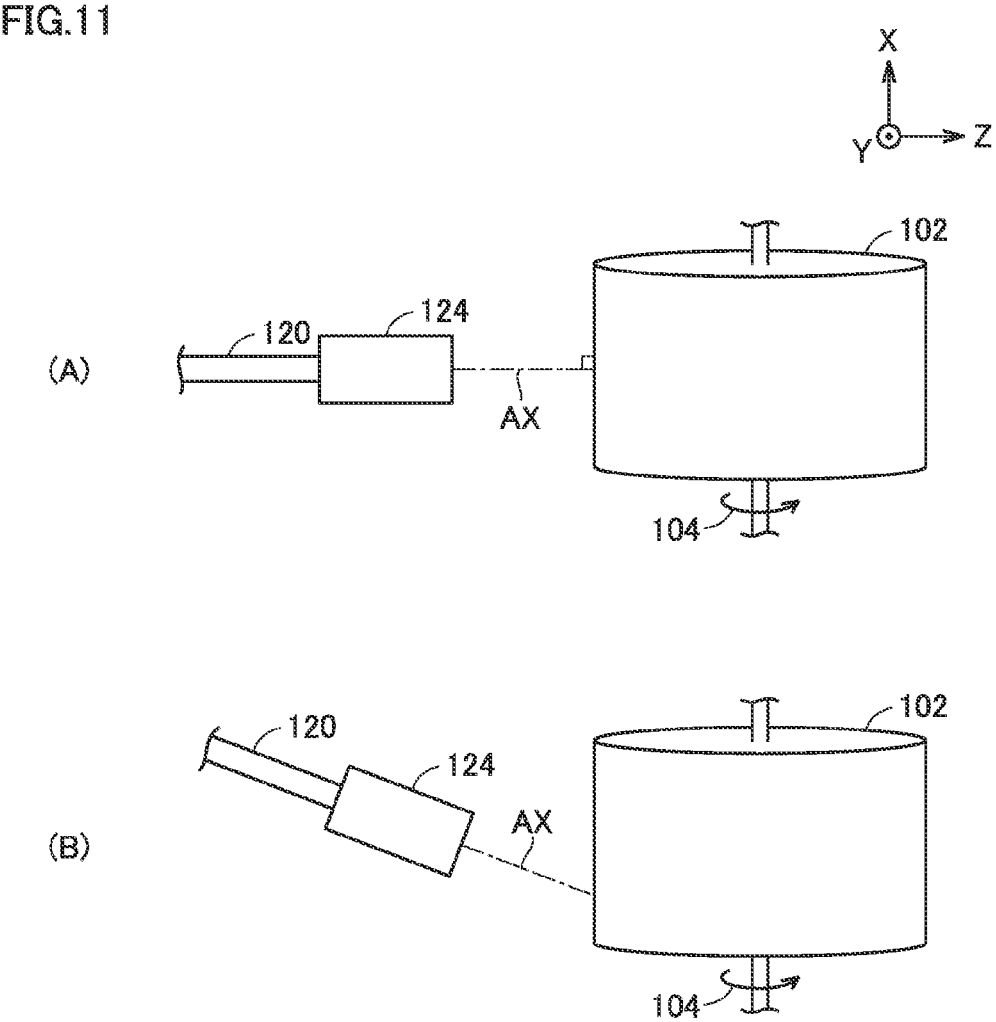
FIG. 11 is a diagram for illustrating a function of a fiber probe used for a film deposition system according to the present embodiment.
Figure 12:
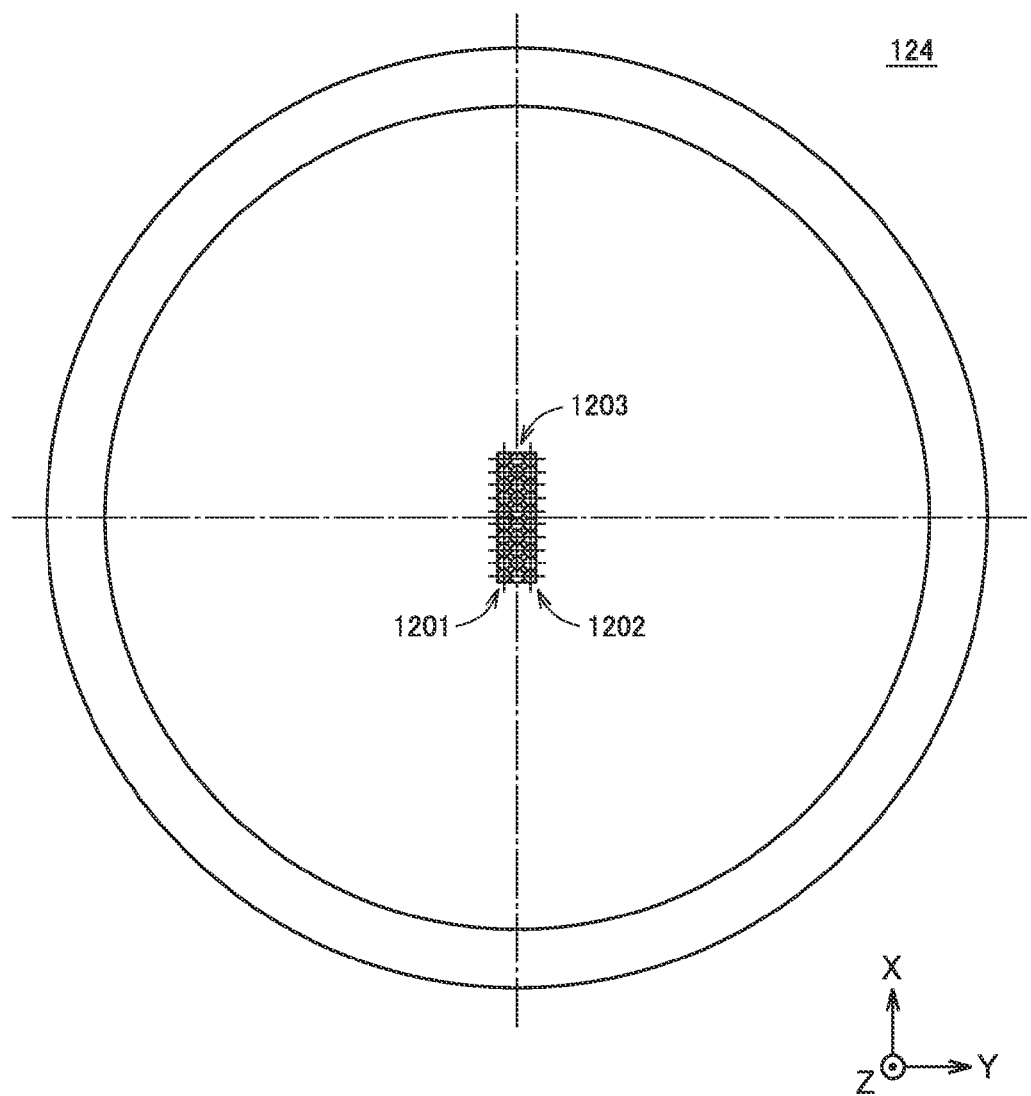
FIG. 12 is a schematic diagram showing a cross-sectional structure of the fiber probe used for the film deposition system according to the present embodiment.

FIG. 11 is a diagram for illustrating a function of fiber probe 124 used for film deposition system 1 according to the present embodiment. FIG. 12 is a schematic diagram showing a cross-sectional structure of fiber probe 124 used for film deposition system 1 according to the present embodiment.

Referring to FIG. 11 (A), in the case where an optical axis AX of fiber probe 124 is perpendicular to the side surface of rotary drum 102, both the incident light and the reflected light propagate along optical axis AX and therefore a problem such as reduction of the signal intensity or occurrence of a measurement error is less likely to arise. In contrast, in the case where optical axis AX of fiber probe 124 is not perpendicular to the side surface of rotary drum 102 as shown in FIG. 11 (B), the incident light applied from fiber probe 124 and the reflected light reflected from sample 2 do not propagate through the same optical path. Further, since rotary drum 102 is rotating, the optical positional relation with fiber probe 124 may vary. It is preferable to employ fiber probe 124 with which stable measurement can be done even when the optical positional relation is deviated.

Referring to FIG. 12, fiber probe 124 of the present embodiment includes primary-coated-fiber groups 1201, 1202, 1203 made up of a plurality of primary coated fibers and arranged along the axial direction (direction in which rotational shaft 104 extends) of rotary drum 102. For example, primary-coated-fiber groups 1201 and 1202 are used as light guide paths for applying the incident light, and primary-coated-fiber group 1203 is used as a light guide path for receiving the reflected light.

Primary-coated-fiber groups 1201 and 1202 are optically connected to optical fiber 212 of optical measurement unit 200. Primary-coated-fiber groups 1201 and 1202 correspond to a first group of optical fibers having respective end faces arranged along the axial direction of rotary drum 102 and optically connected to light source 202.

Primary-coated-fiber group 1203 is optically connected to optical fiber 214 or optical fiber 216 of optical measurement unit 200. Primary-coated-fiber group 1203 corresponds to a second group of optical fibers having respective end faces arranged along the axial direction of the rotary body and optically connected to polychromator 204 or photosensor 206.

In the example shown in FIG. 12, primary-coated-fiber groups 1201, 1202, 1203 are each made up of ten primary coated fibers. For example, a primary coated fiber having a diameter of 230 μm is used.

As shown in FIG. 12, a plurality of primary coated fibers can be arranged along the axial direction of rotary drum 102 to stably measure optical characteristics even when fluctuations due to rotation of rotary drum 102 or fluctuations due to attachment of fiber probe 124 occur.

<E. Second Measurement Method>

Regarding the first measurement method, the method is illustrated above according to which the synchronization timing of polychromator 204 is determined based on the result of output from photosensor 206 in the pre-measurement (1). In contrast, in the case where the rotational speed of rotary drum 102 varies (namely in the case where the rotational speed is not constant), it is preferable to determine the synchronization timing using the result of output between polychromator 204 and photosensor 206, in consideration of the variation of the rotational speed. In the following, a description will be given of a measurement method with which the influence of the variation of the rotational speed of rotary drum 102 can be suppressed.

<<e1: Overview>>

The second measurement method also includes two kinds of measurement procedures: preliminary measurement for acquiring timing information 324 which depends on the position where sample 2 is arranged on rotary drum 102 (pre-measurement); and primary measurement for acquiring an optical characteristic of each sample 2 (primary measurement). Further, the pre-measurement includes two stages of measurement procedures (pre-measurement (1) and pre-measurement (2)). By the pre-measurement, the timing when pulsed incident light is applied by light source 202 and the timing when measurement by polychromator 204 is enabled are determined.

Figure 13:
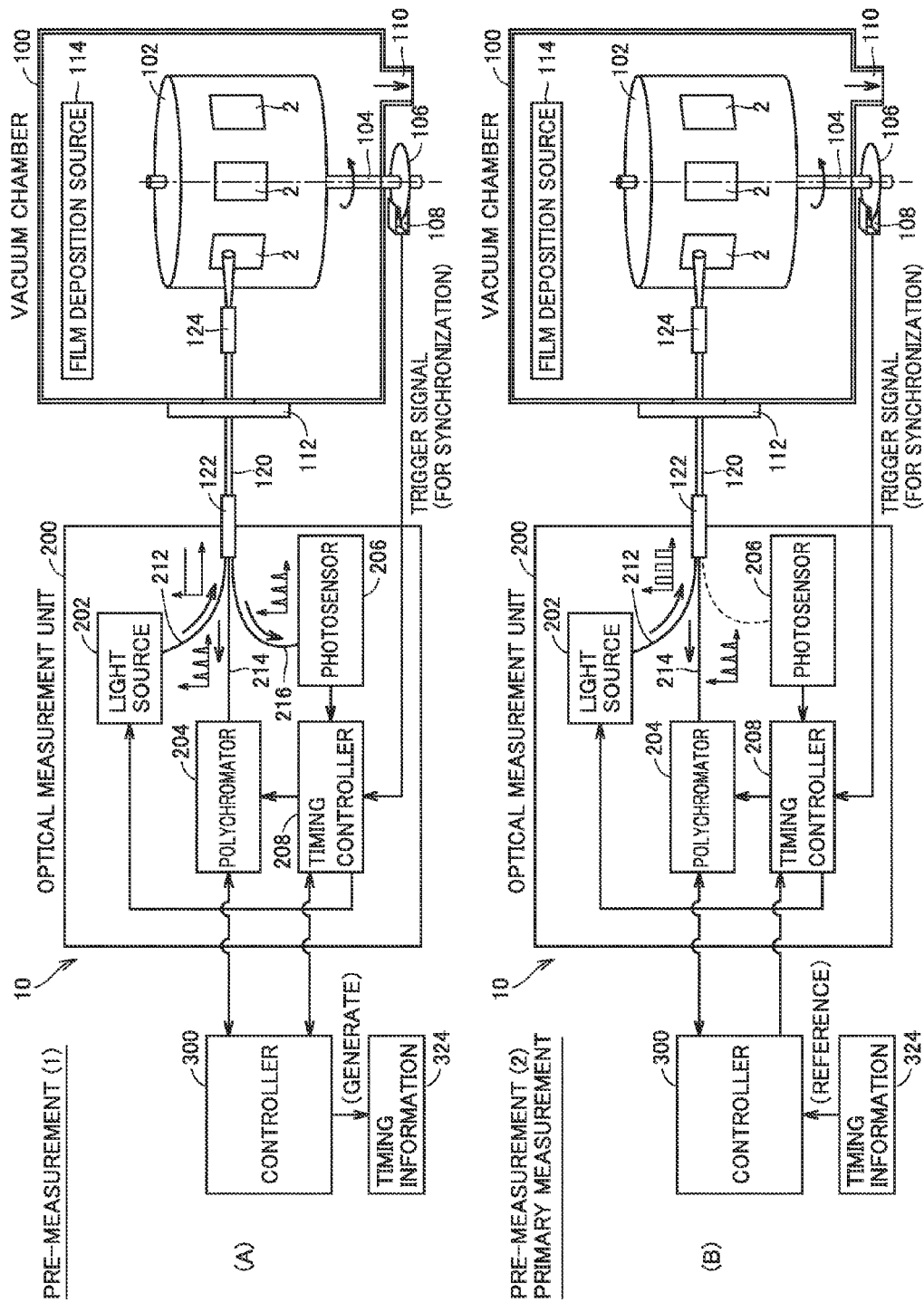
FIG. 13 is a schematic diagram for illustrating a second measurement method according to the present embodiment.

FIG. 13 is a schematic diagram for illustrating the second measurement method according to the present embodiment. In FIG. 13 (A), a relation of connection for the pre-measurement (1) is shown. In FIG. 13 (B), a relation of connection for the pre-measurement (2) and the primary measurement is shown.

According to the pre-measurement (1) of the second measurement method shown in FIG. 13 (A), in contrast to the pre-measurement (1) of the first measurement method shown in FIG. 3 (A), not only photosensor 206 but also polychromator 204 is optically connected to vacuum chamber 100. Namely continuous incident light is generated from light source 202, the continuously generated incident light is reflected from the side surface of rotary drum 102, and the resultant light enters each of polychromator 204 and photosensor 206. It should be noted that the optical path through which the reflected light propagates to enter polychromator 204 is different from the optical path through which the reflected light propagates to enter photosensor 206.

Figure 14:
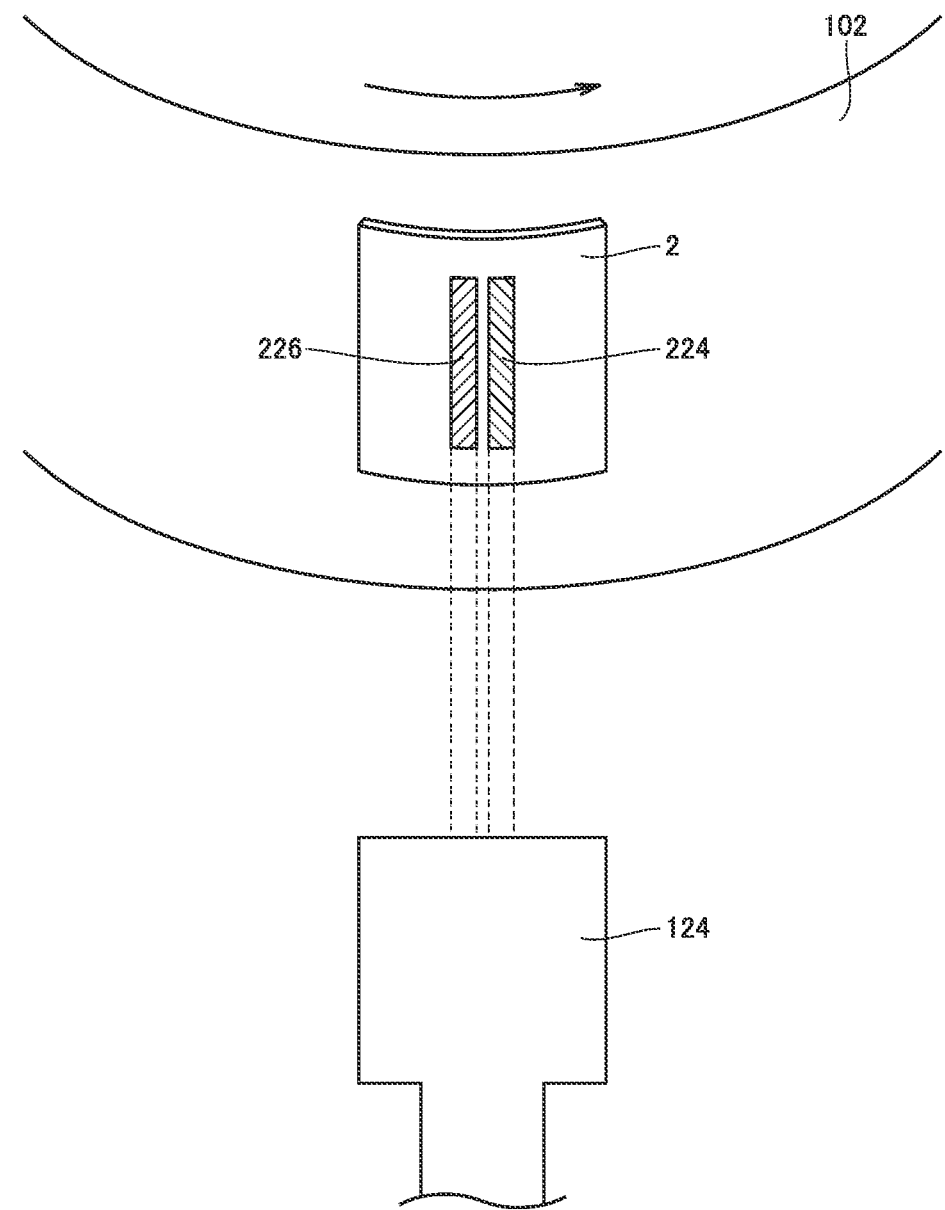
FIG. 14 is a schematic diagram showing incident light applied from a fiber probe of the second measurement method according to the present embodiment.

FIG. 14 is a schematic diagram showing incident light applied from fiber probe 124 of the second measurement method according to the present embodiment. Referring to FIG. 14, a part of the incident light applied from an irradiation opening of fiber probe 124 is incident on an irradiation region 226 located on the side surface of rotary drum 102. The light is reflected from irradiation region 226 and the resultant reflected light enters polychromator 204 through fiber probe 124. Another part of the incident light applied from another irradiation opening of fiber probe 124 is incident on an irradiation region 224 located on the side surface of rotary drum 102. The light is reflected from irradiation region 224 and the resultant reflected light enters photosensor 206 through fiber probe 124.

Because of this difference in optical path, there is a difference in positional relation between irradiation region 224 and irradiation region 226. Due to this, a timing deviation (delay time) is generated between the result of output from polychromator 204 and the result of output from photosensor 206. This delay time should essentially be a constant value which is determined depending on the physical structure of fiber probe 124. However, in the case where the rotational speed of rotary drum 102 varies, this timing deviation (delay time) also varies as the rotational speed varies. The rotational speed of rotary drum 102 may vary in one cycle or over a longer period of time as a film deposition process proceeds.

According to the second measurement method, a time difference between a response of polychromator 204 to reflected light and a response of photosensor 206 to the same reflected light is statistically processed to calculate the deviation (delay time) of the synchronization timing between polychromator 204 and photosensor 206. This deviation of the synchronization timing is used to determine the synchronization timing at which measurement by polychromator 204 is enabled. In the following a more detailed procedure will be described.

<<e2: Pre-Measurement (1)>>

By the pre-measurement (1) of the second measurement method, a timing table for driving photosensor 206 in a synchronized manner that is associated with the position where each sample 2 is arranged is generated. Then, a deviation (delay time) of the synchronization timing between polychromator 204 and photosensor 206 is calculated. Finally, the synchronization timing at which measurement by polychromator 204 is enabled is determined.

When the pre-measurement (1) is performed, the speed of rotary drum 102 is kept at a specified rotational speed as done when the primary measurement is done. Therefore, the intensity of the reflected light detected by photosensor 206 varies with time, depending on the position where sample 2 is arranged on the side surface of rotary drum 102. Based on the variation with time of the intensity of the reflected light, a timing table indicating the position of sample 2 arranged on rotary drum 102 is generated. More specifically, as shown in above-described FIG. 4, offset time T1, T2, T3, . . . is acquired which is a relative time difference, from a reference point, of each point providing the maximum intensity of the reflected light. For the second measurement method, offset time T1, T2, T3, . . . is used as the synchronization timing of photosensor 206, that is associated with the position where each sample 2 is arranged.

Subsequently, the deviation (delay time) of the synchronization timing between polychromator 204 and photosensor 206 is calculated. While the deviation of the synchronization timing may be calculated for each sample 2 arranged on the side surface of rotary drum 102, the following description is of a process example for calculating the deviation of the synchronization timing, based on one sample 2 (typically sample 2 arranged at the position closest to the reference point of rotary drum 102).

Figure 15:
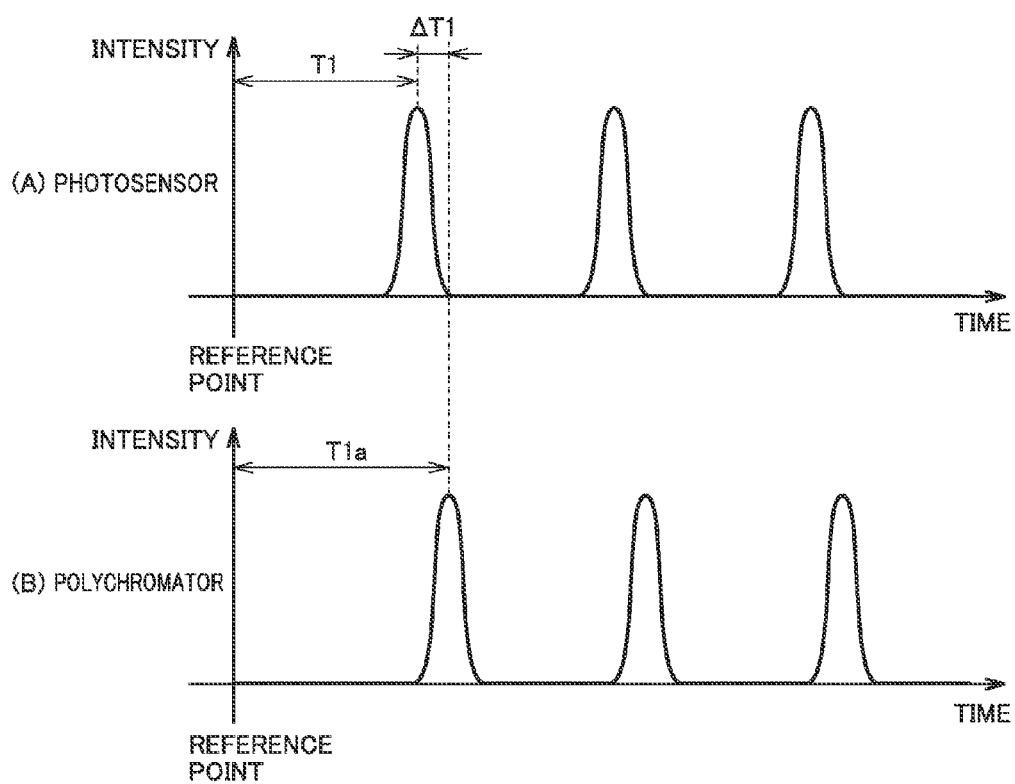
FIG. 15 is a diagram for illustrating details of pre-measurement (1) of the second measurement method according to the present embodiment.

FIG. 15 is a diagram for illustrating details of the pre-measurement (1) of the second measurement method according to the present embodiment. In FIG. 15 (A), an example of the time waveform of the result of output from photosensor 206 in the condition shown in FIG. 13 (A) is shown. In FIG. 15 (B), an example of the time waveform of the result of output from polychromator 204 in the condition shown in FIG. 13 (A) is shown.

A time difference ΔT1 (n) between the position where the intensity of the result of output is the maximum intensity in FIG. 15 (A) (the position located away from the reference point by offset time T1) and the position where the intensity of the result of output is the maximum intensity in FIG. 15 (B) (the position located away from the reference point by offset time T1a) (time difference=T1a−T1) is calculated a predetermined number of times. Then, the calculated N time differences ΔT1 (n) (1≤n≤N) undergo statistical processing to thereby calculate the deviation (delay time) of the synchronization timing between polychromator 204 and photosensor 206. The statistical processing may be simple averaging processing or processing for which reliability is taken into consideration. Further, processing for excluding outliers from the population of time differences ΔT1 (n) may be added to enhance the reliability of the statistics.

By the above pre-measurement (1), the deviation (delay time) of the synchronization timing between polychromator 204 and photosensor 206 is calculated. Then, from offset time T1, T2, T3, . . . which is the synchronization timing of photosensor 206 and time difference ΔT1, the offset time (T1+ΔT1), (T2+ΔT1), (T3+ΔT1), . . . which is the synchronization timing of polychromator 204 is calculated.

Namely, according to the pre-measurement (1), the incident light of a constant intensity generated by light source 202 is applied to an irradiation region which is a region where sample 2 passes as rotary drum 102 rotates, and the reflected light (or transmitted light as will be described later herein) of the applied incident light is received by photosensor 206 and also received by polychromator 204. Based on the deviation of time (delay time) between the output from polychromator 204 and the output from photosensor 206 for the same sample, offset time T1, T2, T3, . . . (first timing information) is corrected. Such pre-measurement (1) can be employed to more accurately determine the synchronization timing of polychromator 204 even when the rotational speed of rotary drum 102 varies.

<<e3: Pre-Measurement (2)>>

By the pre-measurement (2) of the second measurement method, the timing is determined of pulsed incident light with which most efficient measurement can be done when measurement by polychromator 204 is enabled in accordance with the synchronization timing determined by the pre-measurement (1).

Details of processing for this pre-measurement (2) are similar to those of the pre-measurement (2) of the first measurement method, and therefore, the detailed description will not be repeated.

<<e4: Primary Measurement>>

Using timing information 324 acquired through the above-described pre-measurement, the primary measurement is performed. Details of processing for the primary measurement are also similar to those of the primary measurement of the first measurement method as described above, and therefore, the detailed description will not be repeated.

<<e5: Process Procedure>>

Figure 16:
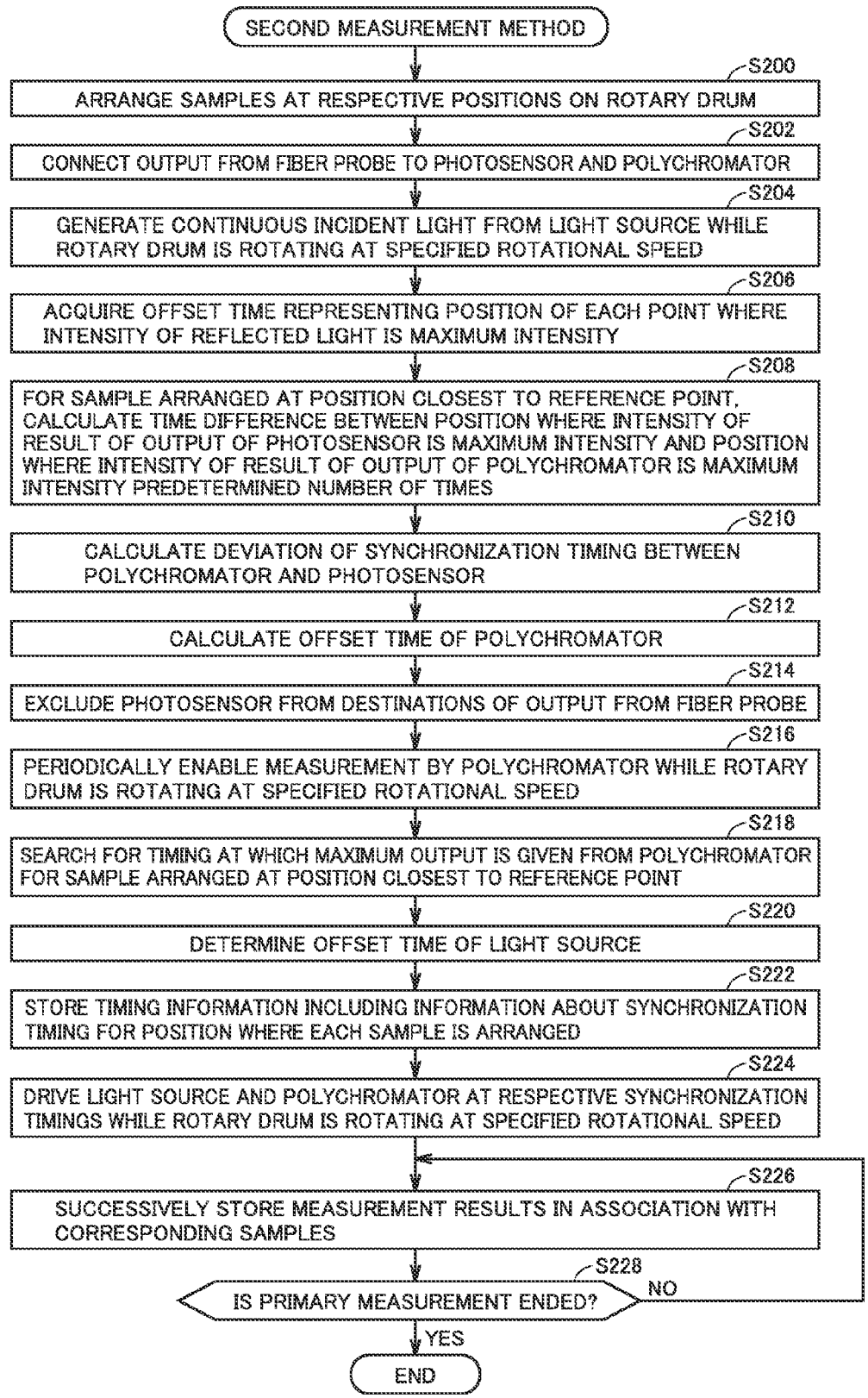
FIG. 16 is a flowchart showing a process procedure of the second measurement method according to the present embodiment.

FIG. 16 is a flowchart showing a process procedure of the second measurement method according to the present embodiment. Referring to FIG. 16, preparation for measurement is done first. More specifically, an operator arranges samples 2 (typically substrates on which films have not been deposited yet) at respective positions on rotary drum 102 (step S200). Subsequently, the operator connects an output from fiber probe 122 to photosensor 206 and also to polychromator 204 in optical measurement unit 200 (step S202). It should be noted that the operations in step S200 and S202 may be performed automatically by a dedicated apparatus or the like.

After this, an instruction to start the pre-measurement (1) is given. Then, in a condition that rotary drum 102 is rotating at a specified rotational speed which is the same condition as the primary measurement (namely the condition when a film deposition process is performed on sample 2), controller 300 causes light source 202 to generate continuous incident light (step S204). Controller 300 acquires offset time T1, T2, T3, . . . representing the position of each point which provides the maximum intensity of the reflected light received by photosensor 206 (step S206). From acquired offset time T1, T2, T3, . . . , the synchronization timing of photosensor 206 is acquired, for the position where each sample 2 is arranged with respect to a reference point of rotary drum 102.

Subsequently, with the condition of the pre-measurement (1) maintained, controller 300 calculates, for sample 2 (first sample) arranged at the position closest to the reference point of rotary drum 102, the time difference between the position (offset time) where the intensity of the result of output of photosensor 206 is the maximum intensity and the position (offset time) where the intensity of the result of output of polychromator 204 is the maximum intensity a predetermined number of times (step S208). Then, controller 300 performs statistical processing on the time differences corresponding to the predetermined number of times that are calculated in step S208 to calculate the deviation (time difference ΔT1 corresponding to the delay time) of the synchronization timing between polychromator 204 and photosensor 206 (step S210). Further, from offset time T1, T2, T3, . . . acquired in step S206 and the deviation (time difference ΔT1) of the synchronization timing between polychromator 204 and photosensor 206 calculated in step S210, controller 300 calculates offset time (T1+ΔT1), (T2+ΔT1), (T3+ΔT1), . . . which is the synchronization timing of polychromator 204 (step S212).

Subsequently, preparation for transition to the pre-measurement (2) is done. More specifically, the operator excludes photosensor 206 from destinations of the output from fiber probe 122 in optical measurement unit 200 (step S214). It should be noted that the operation in step S214 may be performed automatically by a dedicated apparatus (such as a switching device for an optical path) or the like.

After this, an instruction to start the pre-measurement (2) is given. Then, in a condition that rotary drum 102 is rotating at a specified rotational speed which is the same condition as the primary measurement (namely the condition when a film deposition process is performed on sample 2), controller 300 periodically enables measurement by polychromator 204 in accordance with the offset time (T1+ΔT1), (T2+ΔT1), (T3+ΔT1), . . . acquired in step S212 (step S216). Then, controller 300 successively varies the timing at which light source 202 applies pulsed light (offset time T1' from the reference point) to search for the maximum output from polychromator 204 for sample 2 (first sample) arranged at the position closest to the reference point of rotary drum 102 (step S218). Namely, it searches for offset time T1' where the output from polychromator 204 is the maximum output. Further, controller 300 calculates the difference between the offset time (T1+

ΔT1) and offset time T1' where the output from polychromator 204 is the maximum output, and allows this difference to be reflected on other offset time (T2+ΔT1), (T3+ΔT1), . . . to thereby determine offset time T1', T2', T3', . . . of light source 202 (step S220). Timing information 324 includes offset time T1', T2', T3', . . . .

From the acquired offset time T1', T2', T3', . . . , the relation of time between the synchronization timing of polychromator 204 and the synchronization timing at which light source 202 generates the incident light is acquired.

Finally, controller 300 stores timing information 324 including information about the synchronization timing, for the position where each sample 2 is arranged, with respect to the reference point of rotary drum 102 (step S222). Timing information 324 includes a time table for measuring each sample 2 in a synchronized manner. More specifically, timing information 324 includes information indicating the synchronization timing when measurement by polychromator 204 is enabled as well as the synchronization timing when light source 202 generates the pulsed incident light.

After this, an instruction to start the primary measurement is given. Then, in a condition that rotary drum 102 is rotating at a specified rotational speed, controller 300 drives light source 202 and polychromator 204 at respective synchronization timings, with reference to timing information 324 (step S224), and successively stores, in association with corresponding samples 2, the results of measurement which are output from polychromator 204 for respective samples 2 (step S226). This measurement process is repeated until an instruction to end the primary measurement is given (NO in step S228).

<<e6: Structure of Fiber Probe>>

Next, a structure of fiber probe 124 arranged in vacuum chamber 100 will be described. For the second measurement method as well, it is preferable to employ a structure with which the influence of the variation of the optical positional relation of fiber probe 124 with respect to rotary drum 102 can be reduced, as described above with reference to FIG. 11.

Figure 17:
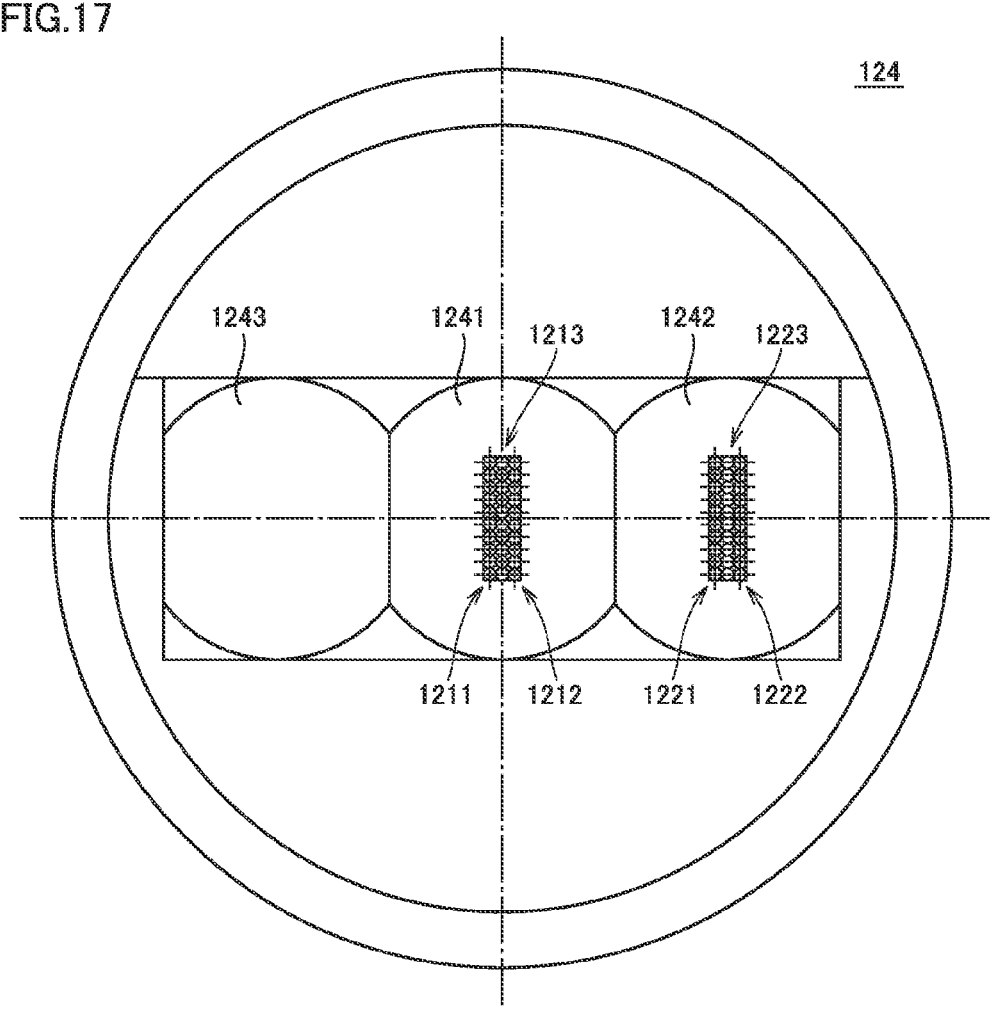
FIG. 17 is a schematic diagram showing another cross-sectional structure of a fiber probe used for a film deposition system according to the present embodiment.

FIG. 17 is a schematic diagram showing another cross-sectional structure of fiber probe 124 used for film deposition system 1 according to the present embodiment. Referring to FIG. 17, fiber probe 124 of the present embodiment includes three sleeves 1241, 1242, 1243. Sleeve 1241 includes a light guide path for the light used for measurement by polychromator 204, of the incident light applied from light source 202. Sleeve 1242 includes a light guide path for the light used for detection by photosensor 206, of the incident light applied from light source 202. It should be noted that sleeve 1243 is arranged as a dummy for stabilizing the shapes of bundle fiber 120 and fiber probe 124.

In sleeve 1241, primary-coated-fiber groups 1211, 1212, 1213 made up of a plurality of primary coated fibers are arranged along the axial direction (direction in which rotational shaft 104 extends) of rotary drum 102. For example, primary-coated-fiber groups 1211 and 1212 are used as light guide paths for applying the incident light, and primary-coated-fiber group 1213 is used as a light guide path for receiving the reflected light. Primary-coated-fiber groups 1211 and 1212 are optically connected to light source 202 through optical fiber 212 of optical measurement unit 200. Primary-coated-fiber groups 1211 and 1212 correspond to a first group of optical fibers having respective end faces arranged along the axial direction of rotary drum 102 and optically connected to light source 202. Primary-coated-fiber group 1213 is optically connected to polychromator 204 through optical fiber 214 of optical measurement unit 200. Primary-coated-fiber group 1213 corresponds to a second group of optical fibers having respective end faces arranged along the axial direction of the rotary body and optically connected to polychromator 204.

Similarly, in sleeve 1242, primary-coated-fiber groups 1221, 1222, 1223 made up of a plurality of primary coated fibers are arranged along the axial direction (direction in which rotational shaft 104 extends) of rotary drum 102. For example, primary-coated-fiber groups 1221 and 1222 are used as light guide paths for applying the incident light, and primary-coated-fiber group 1223 is used as a light guide path for receiving the reflected light. Primary-coated-fiber groups 1221 and 1222 are optically connected to light source 202 through optical fiber 212 of optical measurement unit 200. Primary-coated-fiber groups 1221 and 1222 correspond to a first group of optical fibers having respective end faces arranged along the axial direction of rotary drum 102 and optically connected to light source 202. Primary-coated-fiber group 1223 is optically connected to photosensor 206 through optical fiber 216 of optical measurement unit 200. Primary-coated-fiber group 1223 corresponds to a second group of optical fibers having respective end faces arranged along the axial direction of the rotary body and optically connected to photosensor 206.

As shown in FIG. 17, a plurality of primary coated fibers can be arranged along the axial direction of rotary drum 102 to stably measure optical characteristics even when fluctuations due to rotation of rotary drum 102 or fluctuations due to attachment of fiber probe 124 occur.

<F. Modifications>

<<f1: Transmission Type>>

Regarding the above-described first measurement method and second measurement method, the case where the reflection-type measurement system is used is illustrated for the sake of convenience of description. The methods, however, are also applicable to a transmission-type measurement system.

Figure 18:
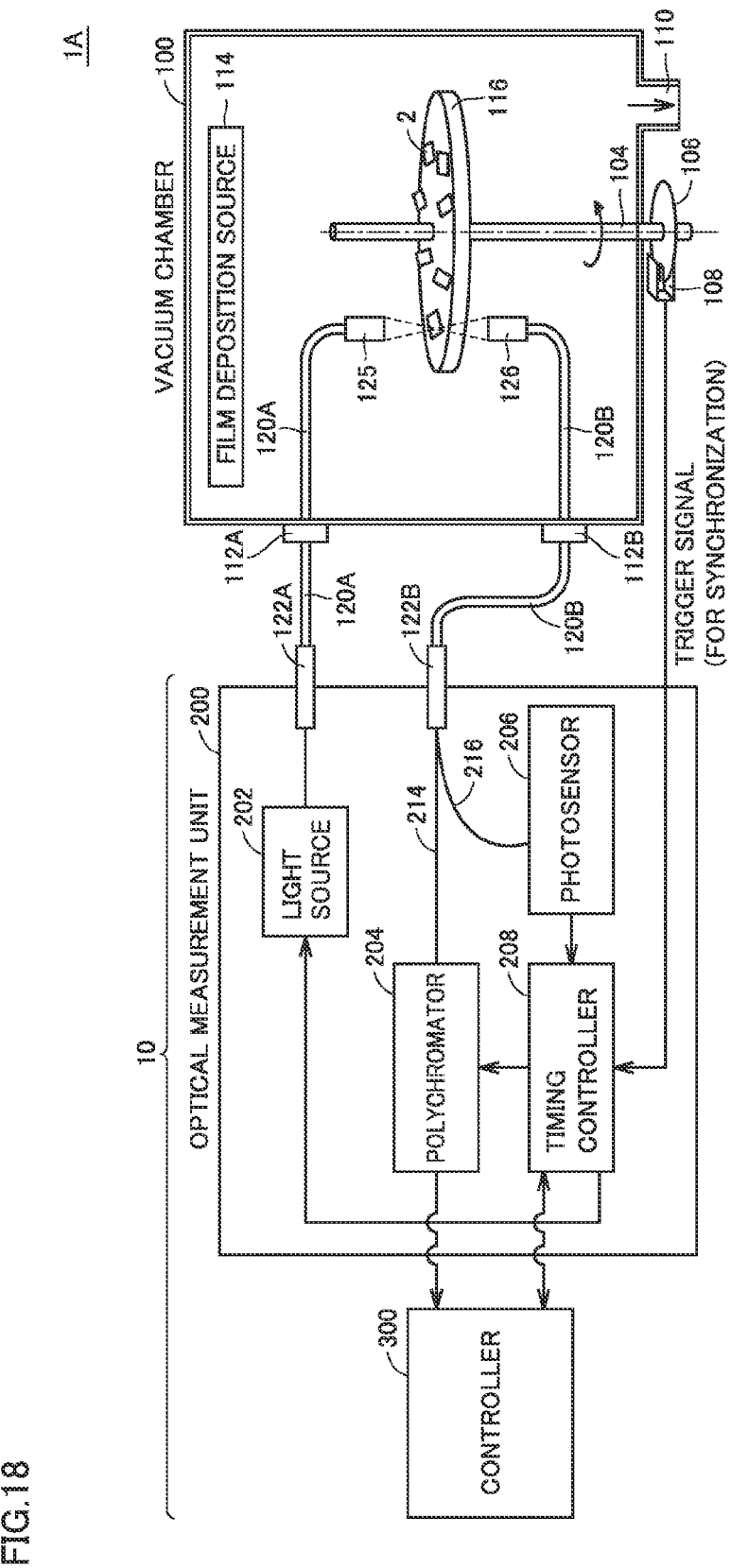
FIG. 18 is a schematic diagram showing a configuration of a film deposition system including an optical measurement apparatus according to the present embodiment.

FIG. 18 is a schematic diagram showing a configuration of a film deposition system 1A including optical measurement apparatus 10 according to the present embodiment. Referring to FIG. 18, in vacuum chamber 100 of film deposition system 1A, a rotary stage 116 which is a rotary body rotatably driven by a drive mechanism (not shown) is arranged. On one circular surface of rotary stage 116, one or a plurality of samples 2 are arranged.

A fiber probe 125 and a fiber probe 126 are arranged above and below rotary stage 116, respectively. Respective optical axes of fiber probe 125 and fiber probe 126 are positionally aligned so that the axes form a common optical axis.

Fiber probe 125 is optically connected to light source 202 through a bundle fiber 120A and a fiber probe 122A. Bundle fiber 120A is arranged through a window 112A of vacuum chamber 100. Fiber probe 126 is optically connected to polychromator 204 or photosensor 206 through a bundle fiber 120B and a fiber probe 122B. Bundle fiber 120B is arranged through a window 112B of vacuum chamber 100.

This optical configuration can be employed to apply the incident light generated by light source 202 to sample 2 and receive the light transmitted through sample 2 to thereby measure optical characteristics of sample 2.

The first measurement method or the second measurement method as described above is also applicable even to the transmission-type measurement system as shown in FIG. 18. It should be noted, however, transmission of the incident light is hindered in the region where sample 2 is present, and therefore, when offset time T1, T2, T3, . . . is to be acquired, the position of each point where the intensity of the transmitted light is the minimum intensity should be searched for. As to the features other than this, the processing as described above is applicable, and thus the detailed description thereof will not be repeated.

<<f2: Method for Detecting Reference Position>>

Regarding the above-described embodiment, the configuration for detecting a predetermined position (reference point/home position) of rotary drum 102 by means of rotation detection sensor 108 is illustrated. However, any configuration may be employed as long as the reference point can be detected. For example, a predetermined pattern may be formed on one of the side surface, the upper surface, and the lower surface of rotary drum 102, for example, and the pattern may be optically detected to detect the reference point. One specific example is as follows. On the side surface of rotary drum 102, a reference region having a reflectance different from that of the remaining region may be provided, and an optical sensor having its field of view including the reference region may be arranged to detect the timing at which the reference region passes.

<<f3: Dynamic Update of Time Width>>

Regarding the above embodiment, it is described that each of time width ΔTD of the pulsed light generated by light source 202 and time width ΔTM for which polychromator 204 is enabled is a fixed value which is designed in advance in accordance with relevant parameters. The values of these widths may be changed appropriately depending on the case. For example, depending on the magnitude of variation of measured offset time T1, T2, T3, . . . or offset time T1', T2', T3', . . . , each time width may be extended or shortened. It should be noted that time width ΔTM for polychromator 204 is preferably as long as possible since it influences the detection sensitivity.

<G. Advantages>

The optical measurement method of the present embodiment appropriately controls the timing (or period of time) when light source 202 generates (applies) incident light and the timing (or period of time) when measurement by polychromator 204 is enabled, to thereby individually measure, in situ, optical characteristics of one or multiple samples 2 arranged on the rotating rotary body. Thus, while film deposition is performed on all samples 2, optical characteristics of all the samples can be measured individually. Therefore, the film deposition process can be controlled with high precision while the state of progress of the film deposition is fed back. Since optical characteristics of each workpiece can be measured during production of the workpiece, occurrence of any malfunction can be addressed immediately. Accordingly, the probability that nonconforming items are produced can be reduced and the yield can be improved.

The optical measurement method of the present embodiment can monitor, with high precision, the process of forming a thin film on a substrate by the sputtering method or the like. At this time, even when a workpiece (substrate) undergoing film deposition is moving at a high speed, monitoring can be done for each workpiece.

The optical measurement method of the present embodiment can be implemented basically as long as one predetermined position (reference point/home position) of the rotary body can be detected. This means that even with an existing apparatus implementing the film deposition process, the in-situ measurement for all samples can be implemented with minimum modifications.

Regarding the optical measurement method of the present embodiment, it is unnecessary to regularly arrange samples on the rotary body. Even when samples are arranged at irregular intervals, the samples can be measured individually.

The fiber probe as described above can be employed to optimize application of the incident light and reception of the reflected light even when a sample arranged in the vacuum chamber is inclined relative to the side surface of the rotary body, and accordingly enhance the robustness. Further, since the fiber probe itself can be reduced in size, the space can be saved as well. Moreover, the fiber probe that can implement multiple optical paths can be employed to simultaneously perform measurement by two independent systems, namely polychromator 204 and photosensor 206.

Regarding the optical measurement method of the present embodiment, even when the rotational speed of the rotary body varies, the variation of the rotational speed can be corrected to enable more appropriate measurement.

It should be construed that the embodiment disclosed herein is given by way of illustration in all respects, not by way of limitation. It is intended that the scope of the present invention is defined by claims, not by the description above, and encompasses all modifications and variations equivalent in meaning and scope to the claims.

REFERENCE SIGNS LIST

1, 1A film deposition system; 2 sample; 10 optical measurement apparatus; 100 vacuum chamber; 102 rotary drum; 104 rotational shaft; 106 rotary plate; 108 rotation detection sensor; 110 suction opening; 112, 112A, 112B window; 114 film deposition source; 116 rotary stage; 120, 120A, 120B bundle fiber; 122, 122A, 122B, 124, 125, 126 fiber probe; 200 optical measurement unit; 202 light source; 204 polychromator; 206 photosensor; 208 timing controller; 212, 214, 216 optical fiber; 224, 226 irradiation region; 300 controller; 302 processor; 304 main memory; 306 network interface; 308 measurement-unit interface; 310 input unit; 312 output unit; 314 bus; 320 hard disk; 322 optical measurement program; 324 timing information; 326 measurement result; 1201, 1202, 1203, 1211, 1212, 1213, 1221, 1222, 1223 primary-coated-fiber group; 1241, 1242, 1243 sleeve.

The invention claimed is:

1. An optical measurement apparatus for measuring an optical characteristic of one or a plurality of samples arranged on a rotary body, comprising:
   a light source;
   a first detection unit configured to output a characteristic value of received light;
   a second detection unit having a higher response speed than the first detection unit and configured to output an intensity of received light; and
   a controller configured to:
      cause, in a condition that a rotational speed of the rotary body is controlled so that the rotational speed is a specified value, the light source to generate light having a constant intensity and apply the light to an irradiation region which is a region where the samples pass as the rotary body rotates, and acquire first timing information based on a change with time of an intensity of reflected light or transmitted light that is output from the second detection unit receiving the reflected light or transmitted light of the applied light, the first timing information being used for defining a period of time for which measurement by the first detection unit is enabled in association with a position of each sample;

cause, in a condition that the rotational speed of the rotary body is controlled so that the rotational speed is the specified value, the light source to periodically generate pulsed light in accordance with the first timing information and apply the pulsed light to the irradiation region, and acquire second timing information based on a result which is output from the first detection unit as a result of measurement by the first detection unit periodically enabled in accordance with the first timing information, the second timing information being used for defining a period of time for which the light source generates the pulsed light; and periodically enable, in a condition that the rotational speed of the rotary body is controlled so that the rotational speed is the specified value, measurement by the first detection unit in accordance with the first timing information and cause the light source to periodically generate pulsed light in accordance with the second timing information, to thereby acquire, for each sample, a characteristic value which is output from the first detection unit.

2. The optical measurement apparatus according to claim 1, wherein the controller determines the first timing information from a position of the rotary body where the intensity which is output from the second detection unit has a maximum value or a minimum value.

3. The optical measurement apparatus according to claim 2, wherein the controller causes the light generated by the light source and having a constant intensity to be applied to the irradiation region and causes the reflected light or the transmitted light of the applied light to be received by the second detection unit and further by the first detection unit, and corrects the first timing information based on a time deviation between an output from the first detection unit for a sample and an output from the second detection unit for the sample.

4. The optical measurement apparatus according to claim 1, wherein the controller causes the light source to generate the pulsed light at multiple different timings, and determines, as the second timing information, a timing at which the output from the first detection unit is relatively larger.

5. The optical measurement apparatus according to claim 1, further comprising a position detection unit configured to detect a predetermined position of the rotary body that serves as a reference for defining the first timing information and the second timing information.

6. The optical measurement apparatus according to claim 5, wherein the first timing information and the second timing information are defined using a time elapsed from detection of the predetermined position of the rotary body in a condition that the rotational speed of the rotary body is controlled so that the rotational speed is the specified value.

7. The optical measurement apparatus according to claim 1, further comprising:

a first group of optical fibers having respective end faces arranged along an axial direction of the rotary body and optically connected to the light source; and a second group of optical fibers having respective end faces arranged along the axial direction of the rotary body and optically connected to the first detection unit or the second detection unit.

8. An optical measurement method of measuring, with a detection unit, an optical characteristic of one or a plurality of samples arranged on a rotary body, comprising:

causing, in a condition that a rotational speed of the rotary body is controlled so that the rotational speed is a specified value, a light source to generate light having a constant intensity and apply the light to an irradiation region which is a region where the samples pass as the rotary body rotates, and acquiring first timing information based on a change with time of an intensity of reflected light or transmitted light of the applied light;

causing, in a condition that the rotational speed of the rotary body is controlled so that the rotational speed is the specified value, the light source to periodically generate pulsed light in accordance with the first timing information and apply the pulsed light to the irradiation region, and acquiring second timing information based on a result which is output from the detection unit as a result of measurement by the detection unit periodically enabled in accordance with the first timing information; and periodically enabling, in a condition that the rotational speed of the rotary body is controlled so that the rotational speed is the specified value, measurement by the detection unit in accordance with the first timing information and causing the light source to periodically generate pulsed light in accordance with the second timing information, to thereby acquire, for each sample, a characteristic value which is output from the detection unit.

9. The optical measurement method according to claim 8, wherein the step of acquiring the first timing information includes determining the first timing information from a position of the rotary body where the intensity which is output from the second detection unit has a maximum value or a minimum value.

10. The optical measurement method according to claim 9, further comprising:

causing the reflected light or the transmitted light of the applied light to be received by the second detection unit and further by the first detection unit; and correcting the first timing information based on a time deviation between an output from the first detection unit for a sample and an output from the second detection unit for the sample.

11. The optical measurement method according to claim 8, wherein the step of causing the light source to generate light includes causing the light source to generate the pulsed light at multiple different timings, and the step of acquiring the second timing information includes determining a timing at which the output from the first detection unit is relatively larger.

12. The optical measurement method according to claim 8, further comprising detecting a predetermined position of the rotary body that serves as a reference for defining the first timing information and the second timing information.

13. The optical measurement method according to claim 12, wherein the first timing information and the second timing information are defined using a time elapsed from detection of the predetermined position of the rotary body in a condition that the rotational speed of the rotary body is controlled so that the rotational speed is the specified value.

14. The optical measurement method according to claim 8, wherein
- a first group of optical fibers having respective end faces is arranged along an axial direction of the rotary body and optically connected to the light source, and
- a second group of optical fibers having respective end faces is arranged along the axial direction of the rotary body and optically connected to the first detection unit or the second detection unit.

* * * * *